United States Patent
Tajima

(10) Patent No.: US 9,694,368 B2
(45) Date of Patent: Jul. 4, 2017

(54) MAGNETIC REAGENT, MAGNETIC REAGENT KIT, METHOD FOR TREATING MAGNETIC CARRIERS, AND TREATMENT DEVICE THEREFOR

(75) Inventor: Hideji Tajima, Matsudo (JP)

(73) Assignee: UNIVERSAL BIO RESEARCH CO., LTD., Matsudo-Shi, Chiba (JP)

(*) Notice: Subject to any disclaimer, the term of this patent is extended or adjusted under 35 U.S.C. 154(b) by 1238 days.

(21) Appl. No.: 13/509,232

(22) PCT Filed: Nov. 12, 2010

(86) PCT No.: PCT/JP2010/070241
§ 371 (c)(1),
(2), (4) Date: Aug. 1, 2012

(87) PCT Pub. No.: WO2011/059076
PCT Pub. Date: May 19, 2011

(65) Prior Publication Data
US 2012/0329124 A1    Dec. 27, 2012

(30) Foreign Application Priority Data

Nov. 13, 2009  (JP) .................................. 2009-259613
Jun. 24, 2010  (JP) .................................. 2010-144208

(51) Int. Cl.
*A61K 9/00*       (2006.01)
*B03C 1/015*      (2006.01)
(Continued)

(52) U.S. Cl.
CPC .............. *B03C 1/015* (2013.01); *B03C 1/288* (2013.01); *G01N 33/54326* (2013.01); *B03C 2201/18* (2013.01); *B03C 2201/26* (2013.01)

(58) Field of Classification Search
CPC ...................................................... B03C 1/015
See application file for complete search history.

(56) References Cited

U.S. PATENT DOCUMENTS 6,509,193 B1     1/2003   Tajima
2006/0121612 A1* 6/2006   Tajima ................... C12M 35/02
                                                435/459

FOREIGN PATENT DOCUMENTS

JP       5-203649        8/1993
JP       11-319628       11/1999
(Continued)

OTHER PUBLICATIONS

International Search Report, mailed Feb. 22, 2011, by the ISA/JP, in connection with PCT/JP2010/070241.
(Continued)

*Primary Examiner* — Paul Dickinson
(74) *Attorney, Agent, or Firm* — Haynes and Boone, LLP

(57) ABSTRACT

The present invention relates to a magnetic reagent, a magnetic reagent kit, a method for treating magnetic carriers, and a treatment device therefor, with an object of quickly and efficiently treating magnetic carriers of a micro particle diameter including nanosized magnetic carriers.

The magnetic reagent or magnetic reagent kit includes: a plurality of magnetic carriers which can be magnetized by being exposed to a magnetic field, can be bonded to a predetermined chemical substance or living organism in a liquid, and that have a particle diameter that enables them to be suspended in the liquid; and a plurality of treatment promoting magnetic particles which can be magnetized by being exposed to a magnetic field and thus can have the magnetic carriers adsorbed on the surface thereof, are formed so that they can be moved within the liquid by movement of the liquid or by a magnetic field, and promote a treatment for capturing or re-suspension of the magnetic carriers.

8 Claims, 19 Drawing Sheets

(51) Int. Cl.
*B03C 1/28* (2006.01)
*G01N 33/543* (2006.01)

(56) References Cited

FOREIGN PATENT DOCUMENTS

| JP | 2008-275534 | 11/2008 |
|---|---|---|
| JP | 2009-013207 | 1/2009 |
| JP | 2009 186356 | 8/2009 |
| JP | 2010-214257 | 9/2010 |
| WO | WO 97/31105 | 8/1997 |
| WO | WO 97/44671 | 11/1997 |
| WO | WO 2004/035776 | 4/2004 |
| WO | WO 2008/072149 | 6/2008 |
| WO | WO 2011/059076 | 5/2011 |

OTHER PUBLICATIONS

English Translation of International Preliminary Report on Patentability Chapter II, dated Jun. 4, 2012, in connection with PCT/JP2010/070241, 7 pages.
International Preliminary Report on Patentability Chapter II, dated May 13, 2012, in connection with PCT/JP2010/070241, 19 pages.
Written Opinion of the International Search Authority, dated May 13, 2012, in connection with PCT/JP2010/070241, 8 pages.
English Translation of International Search Report, dated May 19, 2011, in connection with PCT/JP2010/070241, 4 pages.
Supplementary European Search Report, dated Nov. 5, 2015 in connection with EP2500101 (Application No. 10830035), 2 pgs.
European Search Opinion, dated Nov. 16, 2015, in connection with EP2500101 (Application No. 10830035), 8 pgs.

\* cited by examiner

FIG. 13
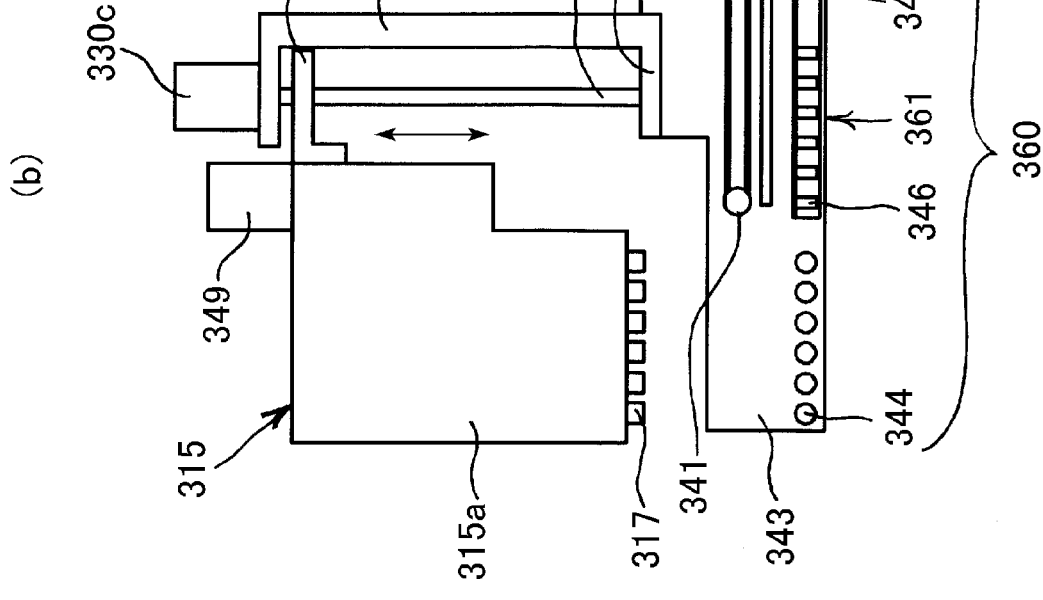
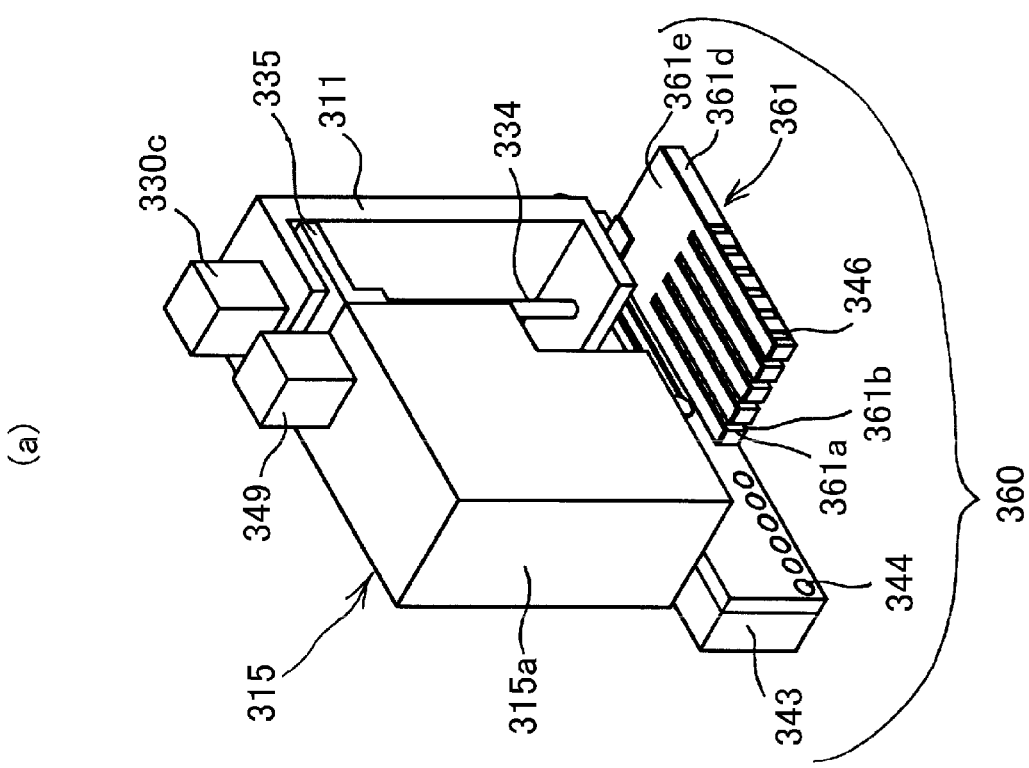

MAGNETIC REAGENT, MAGNETIC REAGENT KIT, METHOD FOR TREATING MAGNETIC CARRIERS, AND TREATMENT DEVICE THEREFOR

CROSS REFERENCE

This application is a United States national phase application of co-pending international patent application number PCT/JP2010/070241, filed Nov. 12, 2010, which claims priority to Japanese patent application number 2009-259613, filed Nov. 13, 2009, and Japanese patent application number 2010-144208, filed Jun. 24, 2010, the disclosures of which are incorporated herein by reference.

TECHNICAL FIELD

The present invention relates to a magnetic reagent, a magnetic reagent kit, a method for treating magnetic carriers, and a treatment device therefor.

BACKGROUND ART

In recent years, in analysis or treatment of a polymer compound such as nucleic acid, protein, and sugar chain, magnetic bodies of a micro particle diameter including extremely minute nano-sized magnetic bodies have been used in order to further increase the solid phase surface area to thereby achieve a higher level of reactivity. Moreover, even with micro-sized living organisms such as cells and bacteria, with magnetic bodies of a micro particle diameter having a certain type of receptor being efficiently bonded to the surface of the biological body, the biological bodies can be covered. By mixing and suspending magnetic bodies of a micro particle diameter with and in a solution containing a target polymer compound or a target living organism in this manner, a treatment such as detection, separation, isolation, and extraction of the target polymer or the target living organism can be performed more efficiently, compared to a treatment that uses magnetic particles of a common micro size (1 to several 100 μm).

If an automated system is available as being provided with a magnet that recovers magnetic bodies by easily and quickly recovering this type of magnetic bodies of a micro particle diameter using an external magnetic field without any need for steps of centrifugal separation and filtration, it will provide a great advantage in a wide range of fields such as isolation and production of DNA and mRNA in the area of genomic research, isolation and production of protein and peptide, and protein-protein interaction analysis in the area of proteomics research, and pharmacologic targeting and pathogenic virus detection in the area of medicine. In particular, an advantage is anticipated in sectors including nucleic acid extraction, peptide extraction, and immunoassay.

However, if the particle diameter of magnetic bodies becomes minute, the magnetic moment possessed thereby and the magnetic flux passing therethrough become smaller. Consequently, there is a problem in that separation and capturing of magnetic bodies requires a larger amount of time, prolonging the amount of time required for a treatment, and it may become difficult to perform a complete separation treatment in a short period of time. For example, in a case where a magnetic field is applied to the interior of a dispensing tip and magnetic bodies are separated by adsorbing them on the inner wall thereof while being suctioned or discharged, since the size of the magnetic flux passing through the magnetic bodies is small, the speed of suction/discharging needs to be lowered and the treatment may require a larger amount of time. Moreover, when suctioning a reagent solution or the like, there is a possibility that magnetic bodies of a micro particle diameter, which should have been adsorbed, may flow out from the dispensing tip. Meanwhile, there is a problem in that when an attempt to adsorb magnetic bodies is made with application of a magnetic field using a powerful magnet, they become agglutinated in a pellet shape more strongly as the particle diameter thereof becomes more minute, and consequently the amount of time required for re-suspension may further increase.

In order to improve these points, there has been practiced a method such that as a polymer composition that becomes responsive depending on temperature, there is used temperature responsive magnetic particles in which a polymer that shows the upper critical solution temperature in a state of being an aqueous solution is fixed on magnetic particles of a particle diameter of 100 nm to 200 nm (Patent Document 1). In this method, the aqueous solution of the temperature responsive magnetic particles is heated, keeping the temperature at not more than the upper critical solution temperature, and the temperature responsive magnetic particles are agglutinated. Then, a magnetic field is applied thereto, and recovery thereof is performed. In this case, for separation of the particles, temperature control needs to be performed with use of a temperature control device, and consequently there is a problem in that the device may become complex and operations may become troublesome, resulting in an increase in the amount of time required for a treatment.

On the other hand, there has been a micro column system in which a porous member manufactured with sintered iron beads is fixed within a column, and by applying a magnetic field to the porous member when a solution containing micro magnetic particles is passing therethrough, these micro magnetic particles are separated (Patent Document 2). In this case, the solution that contains the magnetic particles is flowed unilaterally in the discharging direction of the column, to thereby capture and separate the magnetic particles. Accordingly, in order to completely capture the magnetic particles contained in the solution, it is necessary to dilute the solution or increase the amount of the reagent to thereby increase the amount of the liquid, and to circulate it while pressure is being applied. As a result, there is a problem in that the device may become complex, resulting an increase in the amount of time required for a treatment or in an increase in the amount of the reagent. Furthermore, since the magnetic particles are captured by adsorbing them in several pores of the sintered body fixed within the column, there is a problem in that it may become difficult to perform a treatment in a short period of time in which the sintered body is cleaned by making a cleaning liquid flow thereon, and the magnetic particles that have been re-suspended and further re-suspended in the liquid are concentrated. Moreover, there is a problem in that the porous member is fixed in the column, and it may have a lower chance of encountering magnetic carriers within the liquid, compared to the same amount of particle-shaped members, which are capable of freely moving within the entire liquid.

PRIOR ART DOCUMENTS

Patent Documents

[Patent Document 1] Japanese Unexamined Patent Publication No. 2009-13207

[Patent Document 2] Japanese Unexamined Patent Publication No. H11-319628

SUMMARY OF THE INVENTION

Problems to be Solved by the Invention

Consequently, the present invention has been achieved in order to solve the above problems, and a first aspect thereof is made with an object of providing a magnetic reagent, a magnetic reagent kit, a method for treating magnetic carriers, and a treatment device therefor, capable of quickly and efficiently performing treatments including capturing and re-suspension of magnetic carriers of a micro particle diameter including nanosized magnetic carriers. A second aspect thereof is made with an object of providing a magnetic reagent, a magnetic reagent kit, a method for treating magnetic carriers, and a treatment device therefor, which are suitable for performing various types of treatments for magnetic bodies of a micro particle diameter including nanosized magnetic bodies, using a simple configuration.

Means for Solving the Problem

A first aspect of the invention is a magnetic reagent or a magnetic reagent kit having: a plurality of magnetic carriers which can be magnetized by being exposed to a magnetic field, can be bonded to a predetermined chemical substance or living organism in a liquid, and that have a particle diameter that enables them to be suspended in the liquid; and a plurality of treatment promoting magnetic particles which can be magnetized by being exposed to a magnetic field and thus can have the magnetic carriers adsorbed on a surface thereof, are formed so that they can be moved within the liquid by movement of the liquid or by a magnetic field, and promote a treatment for capturing or re-suspension of the magnetic carriers.

Here, the expression "promotion of a treatment for capturing or re-suspension of the magnetic carriers" refers to reduction in the amount of time required for completing or achieving a state of being close to completion of a treatment for capturing or re-suspending all of the magnetic carriers. The expression "capturing magnetic carriers" refers to separating the magnetic carriers from the liquid, and the expression "re-suspension of magnetic carriers" refers to returning and re-suspending the captured magnetic carriers into the liquid.

"Magnetic carriers" refers to carriers which can be bonded to a predetermined chemical substance or living organism, and have magnetic bodies of a particle diameter which enables the magnetic bodies to be suspended in the liquid. It is preferable that magnetization thereof is performed quickly when being exposed to a magnetic field, and demagnetization is performed quickly when the magnetic field is removed. Examples of this type of material include a super paramagnetic body. Examples of a super paramagnetic body include oxide glass containing magnetic ions, and amorphous ionizable compounds such as fluoride glass. Examples of "bonding" include specific bonding or non-specific bonding, reaction, ion bonding, covalent bonding, and chemical or physical adsorption.

The "predetermined chemical substance or living organism" refers to a so-called treatment target, and examples thereof include: nucleic acids such as DNA and RNA; proteins including an antigen or antibody; biological polymers including amino acids, fats or sugar chains; environmental substances including a dioxin, metal, polymer chloride, or inorganic substance; chemical substances including a toxin; and living organisms such as cells, bacteria, and viruses.

The "particle diameter which enables suspension in the liquid" is, for example, several nano meters to several hundreds micro meters, and more preferably, several nano meters to several tens of micro meters.

The "treatment promoting magnetic particles" are magnetic particles which: without being required to be able to be bonded to a predetermined chemical substance or living organism in a liquid, can be magnetized by a magnetic field when the magnetic field is applied thereto; enable adsorption of the magnetic carriers or the treatment promoting magnetic particles by a magnetic force; and are formed so as to be able to be moved within the liquid by movement of the liquid or by the magnetic field. Therefore, since the treatment promoting magnetic particles can be dispersed or suspended in a liquid by movement of the liquid made, for example, by agitating or shaking the liquid, it is possible, at a close range from the magnetic carriers suspended within the liquid and with a surface area larger than the area of a predetermined capturing region of the inner wall or the like of a container or a tip on which the magnetic carriers are to be adsorbed, to capture the magnetic carriers suspended within the liquid. Moreover, the treatment promoting magnetic carriers can be adsorbed, in a state of the magnetic particles carriers being adsorbed, directly or indirectly on the inner wall of a container or a tip present in the magnetic field direction, by being pulled and moved in the magnetic field direction by the magnetic field (via the treatment promoting magnetic particles or the magnetic carriers). In this manner, the treatment promoting magnetic particles are particles capable of promoting a magnetic carrier capturing (separating) treatment with a magnetic field in which the level of magnetic force to be given to the magnetic carriers is increased compared to the cases where no treatment promoting magnetic particle is present.

In order to achieve this, it is preferable that the treatment promoting magnetic particles are generally of a configuration different from that of the magnetic carriers, and for example, have a different particle diameter or a different material. For example, these treatment promoting magnetic particles have a level of magnetic flux density at least greater than that of the liquid surrounding the particles, and more preferably, they have a greater magnetic flux passing therethrough (they have a greater magnetic moment), or they have a magnetic flux density higher than that of the magnetic carriers. As a result, the magnetic carriers can be attracted by the magnetic force. Moreover, with a greater magnetic flux passing therethrough, the magnetic carriers are strongly magnetized by the applied magnetic field and are attracted even more strongly in the magnetic field direction. As a result, the capturing region area for adsorbing and capturing the magnetic carriers thereon is enlarged from that of the inner wall of a container or a dispensing tip having an area approximately equivalent to simply the area of the magnetic pole of the magnet, to the surface area of the treatment promoting magnetic particles.

Furthermore, the treatment promoting magnetic particles are formed so as to be able to be moved within the liquid by the movement of the liquid or by the magnetic field. Therefore, after having removed the magnetic field, by agitating or shaking the liquid, the treatment promoting magnetic particles, which have been agglutinated when applying a magnetic field once and capturing the magnetic carriers, are re-dispersed or re-suspended to thereby promote dissociation or separation of magnetic carriers from the treatment promoting magnetic carriers, facilitating re-suspension of the magnetic carriers. In this case, although the treatment promoting magnetic particles are of a size sufficiently smaller than that of the container or the dispensing tip which accommodate them, it is preferable that they are formed larger than the magnetic carriers so that they are likely to be influenced by the movement of the liquid.

As described above, preferably, the treatment promoting magnetic particles are formed larger than the magnetic carriers, and are also configured so that a magnetic flux greater than that of the magnetic carriers passes therethrough. Thereby, treatments for capturing and re-suspension of the magnetic carriers both can be promoted.

The size, material, structure (such as single domain, surface processing, and coating), characteristics (such as paramagnetic property, supper paramagnetic property, ferromagnetic property, and ferromagnetic property), and amount of the treatment promoting magnetic particles may be defined according to the purpose of the treatment. Specific examples of the ferromagnetic material of the treatment promoting magnetic particles include an iron-based material, a permalloy-based material, a ferrite-based material, an amorphous-based material, a ferrous hydroxide, a hydrated oxide, a ferric oxide, a composite ferric oxide, and a chrome steel.

Examples of iron-based materials include electromagnetic soft iron (Fe), silicon steel (Fe-3Si), iron-aluminum (Fe-3.5Al), Permendur (Fe-50Co-2V), and Sendust (Fe-9.5Si-5.5Al). Examples of permalloy-based materials include 45 permalloy (Fe-45Ni), 78 permalloy (Fe-78.5Ni), supermalloy (Fe-79Ni-5Mo), mumetal (Fe-77Ni-2Cr-5Cu), and hardperm (Fe-79Ni-9Nb).

Examples of ferrite-based materials include Mn—Zn ferrite (30MnO-17ZnO-51$Fe_2O_3$), Ni—Zn ferrite (15NiO-35ZnO-51$Fe_2O_3$), and Cu—Zn ferrite (22.5CuO-27.5ZnO-50$Fe_2O_3$). Examples of amorphous-based materials include Fe group amorphous (Fe-5Si-3B), and Co group amorphous ($Co_{81.8}$—$Fe_{4.2}$—$Ni_{4.2}$—$Si_{10}$—$B_{20}$).

Having being magnetized, the treatment promoting magnetic particles and the magnetic carriers are attracted to and adsorbed on the predetermined capturing region including the inner wall in the interior of the container or the dispensing tip, and also the magnetic carriers are adsorbed on the treatment promoting magnetic particles adsorbed on the inner wall and so forth. Therefore, the capturing region where the magnetic carriers are meant to be adsorbed directly or indirectly is enlarged, and as a result, magnetic carriers are reliably and efficiently separated.

An example of "magnetic reagent" is a reagent solution which contains the plurality of treatment promoting magnetic particles and a plurality of magnetic carriers in the liquid when they are mixed, and an example of "magnetic reagent kit" is a set consisting of a reagent composed of the plurality of treatment promoting magnetic particles and a reagent composed of a plurality of magnetic carriers, a set consisting of reagent solutions containing either one or both of these, or a set consisting of a reagent and a reagent solution.

Here, it is preferable that these treatment promoting magnetic particles are formed with a material which cannot be bonded to the predetermined chemical substance or living organism, or they are processed so as to be coated with this material. This is because in order to prevent the target from bonding to a material of a certain type of iron based on the non-specific bonding property of the target such as DNA, it is preferable that the surfaces of the treatment promoting magnetic particles are processed so as to be coated with a substance with no non-specific bonding property. Thereby, it is possible to increase the bonding capability of the magnetic carriers themselves. Or, it is preferable by means of another processing to increase the capability of the magnetic carriers to dissociate or separate from the treatment promoting magnetic particles.

A second aspect of the invention is a magnetic reagent or a magnetic reagent kit in which a particle diameter of the treatment promoting magnetic particles is greater than that of the magnetic carriers.

In the case where the treatment promoting magnetic particles have a magnetic flux density at least greater than that of the liquid in which the treatment promoting magnetic particles are suspended, a magnetic field occurs, and compared to those cases where no magnetic field is present, the magnetic carriers are attracted to or adsorbed on the surface of the treatment promoting magnetic particles, or these treatment promoting magnetic particles themselves are pulled in the magnetic field direction and are adsorbed in the predetermined capturing region, thereby promoting the capturing (separating) treatment. In particular, the treatment promoting magnetic particles have a magnetic moment greater than that of the magnetic carriers in the case where a magnetic flux greater than that of the magnetic carriers passes with respect to the same magnetic field. As a result, with respect to the same magnetic field, the treatment promoting magnetic particles receive a greater level of magnetic force or cause it to occur with respect to the magnetic field, compared to the magnetic carriers. Since the treatment promoting magnetic particles are each formed in a particle form which enables movement thereof, they are attracted or adsorbed by a great level of force with respect to the magnetic field in the magnetic field direction within a container or a flow tube such as dispensing tip, and the treatment promoting magnetic particles cause the magnetic carriers, which are smaller than themselves, to be attracted or adsorbed on the surface thereof. When the particle diameter is large, the magnetic carriers and the treatment promoting magnetic particles may be of the same material.

A third aspect of the invention is a magnetic reagent or a magnetic reagent kit in which the particle diameter of the treatment promoting magnetic particles is in a range of 0.001 mm to 5 mm, and the particle diameter of the magnetic carriers is in a range of several nm to several tens of μm.

In the case where the dispensing tip is capable of suction and discharging the treatment promoting magnetic particles, the particle diameter of the treatment promoting magnetic particles is preferably smaller than the inner diameter of the small-diameter tube or the tip end of the dispensing tip. In this type of case, the particle diameter is for example in a range of 0.001 mm to 0.5 mm. On the other hand, the treatment promoting magnetic particles may be enclosed in the flow tube of the dispensing tip and used. In this type of case, the preferred diameter particle is, for example, in a range of 0.5 mm to 5 mm. In the case of enclosing the treatment promoting magnetic particles in the dispensing tip, these can be moved into the small-diameter tube thereof by the movement of the liquid or the magnetic field. However, it is preferable that the treatment promoting particles are enclosed in one column form without disturbing the order so as to be sandwiched by stopping parts provided in two locations in the vicinity of both ends of the small-diameter tube, or they are enclosed in the large diameter part with two filters sandwiching them so that they can be moved into the interior thereof by the movement of the liquid or the magnetic field. The liquid can pass through the lower side of the two filters, however, the treatment promoting magnetic particles cannot pass therethrough. On the upper side, there is provided a pore diameter which allows gas to pass therethrough but which does not allow the treatment promoting magnetic particles to pass therethrough, and the two stopping parts are provided so as to have a gap which allows a liquid to pass therethrough, which does not allow the treatment promoting magnetic particles to pass therethrough, and which is not blocked by these particles.

A fourth aspect of the invention is a magnetic reagent or a magnetic reagent kit in which a magnetic susceptibility of the treatment promoting magnetic particles is greater than that of the magnetic carriers at normal temperature. Here, "magnetic permeability" may be used instead of "magnetic susceptibility". Here, "normal temperature" refers to a temperature not more than the Curie temperature of ferromagnetic bodies, ferrimagnetic bodies, and the like.

When the magnetic body is isotropic, magnetization, magnetic flux density, and magnetic field are in the same direction. In this type of case, the magnetic susceptibility is a dimensionless constant defined by the magnetic body, and when the particle diameters of the magnetic carriers and the treatment promoting magnetic particles are the same, the ones with a greater magnetic susceptibility have a greater magnetic flux.

A fifth aspect of the invention is a magnetic reagent or a magnetic reagent kit in which the treatment promoting magnetic particles have a ferromagnetic body, and the magnetic carriers have a paramagnetic body or a super paramagnetic body.

In general, ferromagnetic bodies have greater magnetic susceptibility and are magnetized stronger compared to paramagnetic bodies, super paramagnetic bodies, and ferrimagnetic bodies, and therefore, they are more suitable for treatment promoting magnetic particles, which are meant to be magnetized more strongly than the magnetic carriers. On the other hand, paramagnetic bodies and super paramagnetic bodies generally have a low level of remnant magnetization, and are magnetized when a magnetic field is applied and are demagnetized quickly when the magnetic field is removed. Therefore, re-suspension becomes easier compared to ferromagnetic bodies and they are suitable for magnetic carriers. Also, even ferromagnetic bodies may become super paramagnetic bodies having super paramagnetism if they are an aggregate of micro particles.

A sixth aspect of the invention is a magnetic reagent or a magnetic reagent kit in which the treatment promoting magnetic particles are formed with a size or from a material different from that of the magnetic carriers, and they can be bonded to a predetermined chemical substance or living organism.

Here, the "predetermined chemical substance or living organism" may or may not match with the "predetermined chemical substance or living organism" of the magnetic carriers. When they are matched, it is possible to perform a more efficient target separation overall. When they are different from each other, two treatments can be performed parallelly at the same time. In this case, as with the magnetic carriers, the non-specific bonding property of the treatment promoting magnetic particles is utilized, or a specific bonding surface processing (for example, bonding substance coating) similar to or different from that of the magnetic carriers is performed with the treatment promoting magnetic particles.

A seventh aspect of the invention is a magnetic reagent or a magnetic reagent kit in which the magnetic carriers are accommodated within a liquid accommodating part of a cartridge container having a single or a plurality of liquid accommodating parts, the treatment promoting magnetic particles are accommodated within the single liquid accommodating part of the cartridge container or another liquid accommodating part, and an opening part of the single or plurality of liquid accommodating parts is sealed with a perforatable thin film.

It is preferable that the treatment promoting magnetic particles are accommodated in the liquid accommodating part so that the treatment promoting magnetic particles can be moved by movement of the liquid or an externally applied magnetic field. Moreover, it is preferable that it is formed so that suction/discharging can be performed with respect to the dispensing tip.

An eighth aspect of the invention is a magnetic reagent kit in which: the magnetic carriers are accommodated within at least one liquid accommodating part of a cartridge container having one or a plurality of liquid accommodating parts; the opening part of the liquid accommodating part is sealed with a perforatable thin film; and the treatment promoting magnetic particles are enclosed within a treatment promoting magnetic particle enclosure flow tube having an opening which can be inserted into the liquid accommodating part and which can suction or discharge a liquid, so that the treatment promoting magnetic particles can be moved by movement of the liquid or an externally applied magnetic field.

It is preferable that the "treatment promoting magnetic particle enclosure flow tube" is a treatment promoting magnetic particle enclosure tip to be described later, which is formed as a tip having, in addition to the opening for performing liquid suction/discharging therethrough, another attachment opening, so that it can be used as a dispensing tip attached to a gas suction/discharging nozzle provided on a movable nozzle head. The flow tube may also include a case such as with a column where a liquid flows in one direction. Moreover, there may be a case where the treatment promoting magnetic particles are enclosed in part of the flow tube, and this portion can be attached to or detached from the flow tube.

The cartridge container, in addition to one or a plurality of liquid accommodating parts, may have one or a plurality of tip accommodating parts, and the tip accommodating part may hold a dispensing tip, or a treatment promoting magnetic particle enclosure flow tube having the treatment promoting magnetic particles enclosed therein such as a treatment promoting magnetic particle enclosure tip. Furthermore, it may be held in one tip accommodating part of the cartridge container. Moreover, a perforation tip may be held in another tip accommodating part of the cartridge container.

A ninth aspect of the invention is a method for treating magnetic carriers including: a contact step of bringing into contact: a liquid containing a target consisting of a predetermined chemical substance or living organism; a plurality of magnetic carriers which can be magnetized by being exposed to a magnetic field, can be bonded to the target in the liquid, and that have a particle diameter that enables them to be suspended in the liquid; and a plurality of treatment promoting magnetic particles which can be magnetized by being exposed to a magnetic field and thus can have the magnetic carriers adsorbed on a surface thereof, are formed so that they can be moved within the liquid by movement of the liquid or by the magnetic field, and promote a treatment for capturing or re-suspension of the magnetic carriers; and a capturing step of capturing magnetic carriers by applying a magnetic field and magnetizing the treatment promoting magnetic particles and the magnetic carriers to thereby adsorb the magnetic carriers or the treatment promoting magnetic particles on the surface of the treatment promoting magnetic particles, and by adsorbing the magnetic carriers and the treatment promoting magnetic particles directly or indirectly on a predetermined capturing region.

The contact step above is performed, for example, in a container, within a column through which the liquid is flowed in one direction, or in a dispensing tip for performing liquid suction/discharging. Here, the magnitude of the "magnetic field" is, for example, approximately 1,000 gauss to several thousands gauss, and a commercially available permanent magnet may be used.

In order to "apply a magnetic field", magnetic field application is performed by bringing a permanent magnet, which is provided to be able to move toward or away from a surface, to the vicinity of the side surface or the bottom surface of the container, or to the side surface of the column or the tip. Alternatively, a member, in which a permanent magnet is wrapped with a non-magnetic material such as plastic and resin, may be provided so as to be able to be inserted through the opening of the container or the column, or through the attachment opening part of the nozzle or the tip, and it is inserted through the opening part into the interior, to thereby apply a magnetic field to the interior of the container or the tip. Here, the "capturing region" refers to a region on which the magnetic carriers can be directly adsorbed (captured), and it is the inner wall of the side surface or the inner wall of the bottom surface of the container, the inner wall of the side surface of the flow tube of the tip, or the outer portion of the member. By using the treatment promoting magnetic particles, the effective surface area serving as the capturing region is enlarged, and magnetic carriers are directly adsorbed also on the surface of the treatment promoting magnetic particles that are directly or indirectly adsorbed on the capturing region.

In the contact step or the separation step, by repeating suction/discharging from the tip, the solution is agitated to thereby improve the level of treatment efficiency. After the separation step, if necessary, there may be provided a dissociation step, in which the bonded chemical substance or living organism is dissociated from the magnetic carriers, and a re-suspension step in which in order to re-suspend the magnetic carriers, in a state where the magnetic field has been removed, suction/discharging of the suspension liquid is repeated using the tip, to thereby re-suspend the adsorbed magnetic carriers.

In the contact step, the components are brought into contact as follows: the treatment promoting magnetic particles and the magnetic carriers suctioned using the tip are transferred and discharged into the container which accommodates the target containing solution; the target containing solution suctioned using the tip is transferred and discharged into the container accommodating the treatment promoting magnetic particles and the magnetic carriers; or the target containing solution is suctioned into the tip, on which the treatment promoting magnetic particles and the magnetic carriers have been adsorbed by applying a magnetic field.

A tenth aspect of the invention is a method for treating magnetic carriers further including a re-suspension step of re-suspending the magnetic carriers in the liquid by agitating or shaking the liquid containing the magnetic carriers that have been captured, in a state where the magnetic field has been removed.

An eleventh aspect of the invention is a method for treating magnetic carriers in which a particle diameter of the treatment promoting magnetic particles is greater than the particle diameter of the magnetic carriers.

A twelfth aspect of the invention is a method for treating magnetic carriers in which a magnetic susceptibility of the treatment promoting magnetic particles is greater than a magnetic susceptibility of the magnetic carriers at normal temperature. Therefore, it is preferable for example that the treatment promoting magnetic particles have ferromagnetic bodies, and the magnetic carriers have super paramagnetic bodies or paramagnetic bodies.

A thirteenth aspect of the invention is a method for treating magnetic carriers including: a particle layer formation step of forming a particle layer by deploying magnetic carriers or treatment promoting magnetic particles in a manner such that a magnetic force line is formed so as to pass through one or more tips that perform suction and discharging of a liquid containing at least a plurality of magnetic carriers that can be magnetized by being exposed to a magnetic field, that can be bonded to a target in the liquid, and that have a particle diameter that enables them to be re-suspended in the liquid, and a plurality of the treatment promoting magnetic particles which can be magnetized by being exposed to a magnetic field and thus can have the magnetic carriers adsorbed on a surface thereof, are formed so that they can be moved within the liquid by movement of the liquid or by a magnetic field, and promote a treatment for capturing or re-suspension of the magnetic carriers, and such that the magnetic carriers or the treatment promoting magnetic particles are adsorbed directly or indirectly on the inner wall of the tip, which is the predetermined capturing region, or on the inner wall of the liquid accommodating part, and the tip and the liquid accommodating part are separated; and a passing step of moving a liquid containing a target composed at least of a predetermined chemical substance or living organism so as to pass through the particle layer. This aspect of the invention may be combined with the ninth aspect of the invention. The "particle layer formation step" above is such that a magnetic force line is formed so as to pass through the tip or the liquid accommodating part, and the magnetic carriers are deployed so that the magnetic carriers or the treatment promoting magnetic particles are adsorbed directly or indirectly on the inner wall of the tip, which is the predetermined capturing region, or on the inner wall of the liquid accommodating part, and the tip and the liquid accommodating part are separated. The "passing step" above is such that for example, with use of the tip, suction and discharging of the liquid is performed or repeated in the tip or with respect to the liquid accommodating part.

In order to form a magnetic force line so as to pass through the tip or the liquid accommodating part, for example, two magnets are positioned so as to sandwich the tip or the liquid accommodating part, so that different magnetic poles face each other. With the deployment, the magnetic carriers, the treatment promoting magnetic particles, or a mixture of these form a filter-form particle layer that, for example, vertically separates the tip or the liquid accommodating part. The amount of the magnetic carriers, the treatment promoting magnetic particles, or the mixture of these is defined based on the inner diameter of the liquid accommodating part or the tip so that they can be separated upon the deployment.

A fourteenth aspect of the invention is a method for treating magnetic carriers including: a mixing step of introducing into one or more tips or accommodating in one or more liquid accommodating parts a mixed liquid of at least two types of liquids selected from a group consisting of a liquid containing a target consisting of a predetermined chemical substance or living organism, a liquid containing a plurality of magnetic carriers which can be magnetized by being exposed to a magnetic field, can be bonded to the target in the liquid, and that have a particle diameter that enables them to be suspended in the liquid, and a liquid containing a plurality of the treatment promoting magnetic particles which can be magnetized by being exposed to a magnetic field and thus can have the magnetic carriers adsorbed on a surface thereof, are formed so that they can be moved within the liquid by movement of the liquid or by a magnetic field, and promote a treatment for capturing or re-suspension of the magnetic carriers; and a movement alteration step of altering the movement of the magnetic carriers or the treatment promoting magnetic particles in the liquid by applying an orientation alteration magnetic field to alter the orientation of the magnetic poles of the magnet brought into the vicinity of the tip having the mixed liquid introduced thereinto or the liquid accommodating part having the mixed liquid accommodated therein. This aspect of the invention may be combined with the particle layer formation step or the passing step of the thirteenth aspect of the invention. The "direction alteration" includes a reversal alteration in which the orientation of the magnetic force line passing through the magnetic pole is changed to the reversed orientation.

A fifteenth aspect of the invention is a magnetic carrier treatment device comprising: a container having one or more liquid accommodating parts capable of accommodating various types of reagents; a nozzle head for performing gas suction/discharging, having one or more nozzles provided therewith; one or more tips that are attachably and detachably attached to the nozzle, and that have a tip end provided so as to be able to be inserted into the liquid accommodating part; a movement mechanism which enables relative movements between the nozzle head and the container; and a magnetic force device capable of applying and removing a magnetic field to and from an interior of at least either one of the tip attached to the nozzle and the liquid accommodating parts, wherein: a plurality of magnetic carriers that can be suctioned/discharged by the tip, that can be magnetized by being exposed to a magnetic field, that can be bonded to a predetermined chemical substance or living organism, and that have a particle diameter that enables them to be re-suspended in the liquid, are accommodated in the interior of at least one of the liquid accommodating parts; and a plurality of treatment promoting magnetic particles that are magnetized by being exposed to a magnetic field and thus can have the magnetic carriers adsorbed on a surface thereof, and that promote a treatment of capturing or re-suspension of the magnetic carriers, are accommodated within at least one of the liquid accommodating parts, so that they can be suctioned/discharged by the tip, and they can be moved in the liquid by the movement of the liquid or by the magnetic field, or they are enclosed in at least one of the tips so that they can be moved in the liquid by the movement of the liquid or by the magnetic field. It is preferable that the tip or the tip having the treatment promoting magnetic particles enclosed therein (treatment promoting magnetic particle enclosure tip) is held in a tip accommodating part provided in the container, so as to be able to be attached to the nozzle.

A sixteenth aspect of the invention is a magnetic carrier treatment device further comprising one or more perforation tips that can be attached to the nozzle provided on the nozzle head, wherein each liquid accommodating part of the container is sealed with a thin film that can be perforated by the perforation tip attached to the nozzle. It is preferable that the perforation tip is held in the tip accommodating part of the container, so as to be able to be attached to the nozzle. The container is a prepacked type cartridge container.

A seventeenth aspect of the invention is a magnetic carrier treatment device in which a particle diameter of the treatment promoting magnetic particles is greater than the particle diameter of the magnetic carriers.

An eighteenth aspect of the invention is a magnetic carrier treatment device in which a magnetic susceptibility of the treatment promoting magnetic particles is greater than a magnetic susceptibility of the magnetic carriers at normal temperature.

A nineteenth aspect of the invention is a magnetic carrier treatment device comprising: a container having one or more liquid accommodating parts capable of accommodating various types of reagents; a nozzle head for performing gas suction/discharging, having one or more nozzles provided therewith; one or more tips that are attachably and detachably attached to the nozzle, and that have a tip end provided so as to be able to be inserted into the liquid accommodating part; a movement mechanism which enables relative movements between the nozzle head and the container; and a magnetic force device capable of applying and removing a magnetic field to and from the interior of either one of the tip attached to the nozzle and the liquid accommodating parts, wherein: a plurality of magnetic carriers that can be suctioned/discharged by the tip, that can be magnetized by being exposed to a magnetic field, that can be bonded to a predetermined chemical substance or living organism, and that have a particle diameter that enables them to be re-suspended in the liquid, or a plurality of treatment promoting magnetic particles which can be magnetized by being exposed to a magnetic field and thus can have the magnetic carriers adsorbed on a surface thereof, that promote a treatment for capturing or re-suspension of the magnetic carriers, that can be suctioned/discharged by the tip, and that can be moved in the liquid by the movement of the liquid or the magnetic field, are accommodated within at least one of the liquid accommodating parts; and the magnetic force device is provided with a magnet array member in which a set of corresponding several magnets, provided so as to be able to move relatively to the tip or the liquid accommodating part, and that are capable of concurrently applying and removing a magnetic field to and from the interior of each tip attached to the nozzle or each liquid accommodating part, are arranged so that when in the vicinity of each tip or each liquid accommodating part, different magnetic poles of at least two of the magnets of each set are facing each other and sandwiching the tip or the liquid accommodating part. The magnet array member is preferably such that each of the magnets is provided so as to be able to move along a linear path that does not intersect with the tip or the liquid accommodating part. Here, the "magnet" is a permanent magnet or an electromagnet. However, a permanent magnet is preferred.

A twentieth aspect of the invention is a magnetic carrier treatment device comprising: a container having one or more liquid accommodating parts capable of accommodating various types of reagents; a nozzle head for performing gas suction/discharging, having one or more nozzles provided therewith; one or more tips that are attachably and detachably attached to the nozzle and that have a tip end provided so as to be able to be inserted into the liquid accommodating part; a movement mechanism which enables relative movements between the nozzle head and the container; and a magnetic force device capable of applying and removing a magnetic field to and from the interior of either one of the tip attached to the nozzle and the liquid accommodating parts, wherein: a plurality of magnetic carriers that can be suctioned/discharged by the tip, that can be magnetized by being exposed to a magnetic field, that can be bonded to a predetermined chemical substance or living organism, and that have a particle diameter that enables them to be re-suspended in the liquid, or a plurality of treatment promoting magnetic particles which can be magnetized by being exposed to a magnetic field and thus can have the magnetic carriers adsorbed on a surface thereof, that promote a treatment of capturing or re-suspension of the magnetic carriers, that can be suctioned/discharged by the tip, and that can be moved in the liquid by the movement of the liquid or the magnetic field, are accommodated within at least one of the liquid accommodating parts; and the magnetic force device is provided with: a magnet array member in which a set of one or more magnets corresponding to each one tip or each liquid accommodating part, that are provided so as to be able to move relatively to the tip or the liquid accommodating part, and that are capable of concurrently applying and removing a magnetic field to and from the interior of each tip attached to the nozzle or each liquid accommodating part, are supported so that the orientation of the magnetic poles thereof can be altered; and a magnetic pole orientation alteration device that is capable, by applying an orientation altering magnetic field, of altering the orientation of the magnetic poles of each magnet. Here, the "orientation altering magnetic field" is a magnetic field with a level of intensity sufficient for altering the orientation of the magnetic poles of each magnet. The orientation altering magnetic field of a given magnet is a magnetic field that corresponds to a magnetic force greater than the sum of magnetic forces that this magnet receives from other magnets arranged at the periphery thereof, and the level of intensity of the magnetic field is defined depending on; the magnetic force of each magnet, the arrangement of each magnet including the distance between the magnets, the number of magnets, the shape of each magnet, and the support-state of each magnet. The level of the intensity of this orientation altering magnetic field generally differs from the intensity level of the magnetic field of each magnet. This aspect of the invention may be combined with the nineteenth aspect of the invention. In this case, the orientations of the magnetic poles of the magnets that are facing each other and sandwiching each tip or each liquid accommodating part are altered, and the level of magnetic field alteration effect is high. It is preferable that the orientation alteration of the magnetic poles is performed at a substantially fixed position.

A twenty-first aspect of the invention is a magnetic carrier treatment device, wherein: each of the magnets is formed in a form of a body of rotation; the magnet array member has one or more magnet groups that are arranged at predetermined intervals in a one column form, so that each of the corresponding magnets of each set, with rotation, can perform orientation alterations in a chain-reaction manner at a substantially fixed position; and the magnetic pole orientation alteration device has an electromagnet that, when the magnet array member is moved so that the magnet on the tip end of each magnet group approaches the tip or the liquid accommodating part, alters the magnetic pole of the rear end magnet of each of the groups by applying an orientation altering magnetic field thereto, to thereby alter the magnetic pole of the front end magnet and alter the magnetic field to be applied to the tip or the liquid accommodating part. Here, the "rotation body form" is a three-dimensional shape with a cross-sectional surface perpendicular to the rotational symmetry axis of a circular shape with the axis serving as the center thereof. The "predetermined interval" is an interval that allows the tip or the liquid accommodating part to be sandwiched therein. The electromagnet is provided, for example, on the nozzle head, the magnet array member itself, or the movement mechanism related to the nozzle head. Here, the intensity level and the orientation of the magnetic force generated by the electromagnet are based on the orientation and the amount of the electric current applied to the electromagnet. Moreover, this aspect of the invention may be combined with the nineteenth aspect of the invention, and in this case, the magnets of each set have at least two magnet groups.

It is preferable that: the liquid accommodating parts of the container are arranged in a matrix form; the nozzles are arranged in a matrix form on the nozzle head; all of the tips attached to the nozzles are provided so as to be able to be concurrently inserted into all or some wells of the container; with respect to the nozzle head or the container in which a nozzle row with nozzles arranged along the row direction or a liquid accommodating part row with liquid accommodating parts arranged along the row direction, and a nozzle column with nozzles arranged along the column direction or a liquid accommodating part column with liquid accommodating parts arranged along the column direction, are respectively provided, the magnet array member of the magnetic force device is provided so as to be able to relatively move along the row direction or the column direction; there are provided a plurality of comb tooth members that extend along the row direction or the column direction, at least one of which can be inserted between the nozzle rows or the liquid accommodating rows, or between the nozzle columns or the liquid accommodating columns, and that when inserted, have a shape and size allowing them to be adjacent to all of the tips attached to the nozzles or to the entire liquid accommodating part group, and a base part that is connected to or integrally formed with the comb tooth members; and on each of the comb tooth members, there are provided one or more magnets arranged at the row intervals or column intervals in positions corresponding to each tip or each liquid accommodating part that can be adjacent thereto. Here, the matrix form includes a single row form or a single column form.

Effect of the Invention

According to the first aspect of the invention, the ninth aspect of the invention, or the fifteenth aspect of the invention, magnet carriers that can be bonded to the target within the liquid, together with treatment promoting magnetic particles that can be magnetized with a magnetic field, are brought into contact with the liquid, and then a magnetic field is applied. Thereby, the magnetic carriers and the treatment promoting magnetic particles are magnetized, the magnetic carriers are attracted to or adsorbed on the surface of the treatment promoting magnetic particles, and further, the treatment promoting magnetic particles are directly or indirectly attracted to or adsorbed on the predetermined capturing region of the container or the tip via the magnetic field, thereby enlarging the surface area of the predetermined capturing region. As a result, it is possible to capture the magnetic carriers quickly and efficiently.

Moreover, since the treatment promoting magnetic particles can be moved within the liquid by movement of the liquid or by the magnetic field, the chance of encountering magnetic carriers suspended in the liquid is high, and since the magnetic carriers can be attracted or adsorbed at a close range within the liquid, capturing can be quickly performed at a high level of capturing efficiency.

Furthermore, since the treatment promoting magnetic particles are provided so as to be able to be moved within the liquid by movement of the liquid or by the magnetic field, after having removed the magnetic field, by agitating or shaking the liquid, the treatment promoting magnetic particles, which have been agglutinated when applying a magnetic field once and capturing the magnetic carriers, are re-dispersed or re-suspended. Thereby, it is possible to facilitate re-suspension of the magnetic carriers.

According to the second aspect of the invention, the third aspect of the invention, the eleventh aspect of the invention, or the seventeenth aspect of the invention, since the particle diameter of the treatment promoting magnetic particles is formed greater than that of the magnetic carriers, even in the case where the treatment promoting magnetic particles and the magnetic carriers are formed with the same material, it is possible to efficiently attract and adsorb the magnetic carriers since the magnetic flux is greater. Moreover, by using treatment promoting magnetic particles of a large particle diameter, liquid movement is likely to influence the treatment, and re-suspension can be efficiently performed in a short period of time. Furthermore, since the magnetic carriers and the treatment promoting magnetic particles can be separated by the difference in particle size, it is possible to recycle and repeatedly use the treatment promoting magnetic particles.

According to the fourth aspect of the invention, the twelfth aspect of the invention, or the eighteenth aspect of the invention, even in a case where there are used treatment promoting magnetic particles and magnetic carriers with almost no difference in particle size therebetween, since a large magnetic flux passes through the treatment promoting magnetic particles, even if the same magnetic field as that of the magnetic carriers is received, the magnetic field generates a large magnetic force and the magnetic force is received. As a result, it is possible to quickly and efficiently perform the treatment in the predetermined capturing region. As long as the level of magnetic susceptibility is high, not only ferromagnetic bodies but also super paramagnetic bodies or the like may be used. Furthermore, since the magnetic carriers and the treatment promoting magnetic particles can be separated based on the difference in the level of magnetic flux, it is possible to recycle and repeatedly use the treatment promoting magnetic particles.

According to the fifth aspect of the invention, by using ferromagnetic bodies as the treatment promoting magnetic particles, and by using super paramagnetic bodies or paramagnetic bodies with no or small remnant magnetization, although the magnetic susceptibility is smaller than that of ferromagnetic bodies, it is possible to perform a quick and highly efficient treatment.

According to the sixth aspect of the invention, by providing the treatment promoting magnetic particles as being capable of bonding to a predetermined chemical substance or living organism, it is possible to additionally or parallelly treat a target that matches with the magnetic carriers or a target that differs from the magnetic carriers. At this time, the magnetic carriers and the treatment promoting magnetic particles can be separated by a filter based on the difference in particle diameter, or they can be separated based on the difference in magnetization. Therefore, it is possible to parallelly perform a plurality of treatments, while improving the level of treatment efficiency and reducing the cost of treatment.

According to the seventh aspect of the invention, the eighth the aspect of invention, the fifteenth aspect of the invention, or the sixteenth aspect of the invention, by preliminarily accommodating or enclosing the magnetic carriers and the treatment promoting magnetic particles in the container or tips to be used, it can be made suitable for automation, and it is possible to prevent it from being contacted through human work and to reliably prevent cross contamination.

According to the ninth aspect of the invention or the fifteenth aspect of the invention, by combining with a dispensing machine, it is possible to further increase the chances of encounter and the level of reactivity with magnetic carriers, thereby enabling a quick treatment that is suitable for automation.

According to the tenth aspect of the invention, since the treatment promoting magnetic particles and the magnetic carriers are provided so as to be able to move in the liquid, by agitating or shaking the liquid, the treatment promoting magnetic particles are re-dispersed or re-suspended, and thereby the magnetic carriers can be easily re-suspended.

According to the thirteenth aspect of the invention or the nineteenth aspect of the invention, by forming a magnetic force flux so as to pass through the tips or liquid accommodating parts, the magnetic carriers, the treatment promoting magnetic particles, or a mixture of these are deployed so as to form a filter-form particle layer that separates the tips or container vertically, and for example, using the tip, liquid suction/discharging are performed or repeated vertically so as to pass the liquid through the particle layer. Thereby, it is possible to increase the chances of the magnetic carriers encountering with the chemical substance or living organism, and promote a reaction treatment.

According to the fourteenth aspect of the invention, the twentieth aspect of the invention, or the twenty-first aspect of the invention, by altering the orientation of the magnetic poles of the magnet that applies a magnetic field to the liquid containing the magnetic carriers or the treatment promoting magnetic particles, using an orientation altering magnetic field, the magnetic carriers or the treatment promoting magnetic particles accommodated in the tip or the liquid accommodating part are moved and agitated or shaken. Thereby, it is possible to further increase the chances of the magnetic carriers encountering the target, and promote the reaction treatment. Therefore, this can be realized by applying an orientation altering magnetic field to the magnet without providing a complex mechanism and enlarging the scale of the device.

BRIEF DESCRIPTION OF THE DRAWINGS

FIG. 13 is a diagram showing a nozzle head of the magnetic carrier treatment device according to the fourth embodiment of the present invention.

BEST MODE FOR CARRYING OUT THE INVENTION

Figure 1:
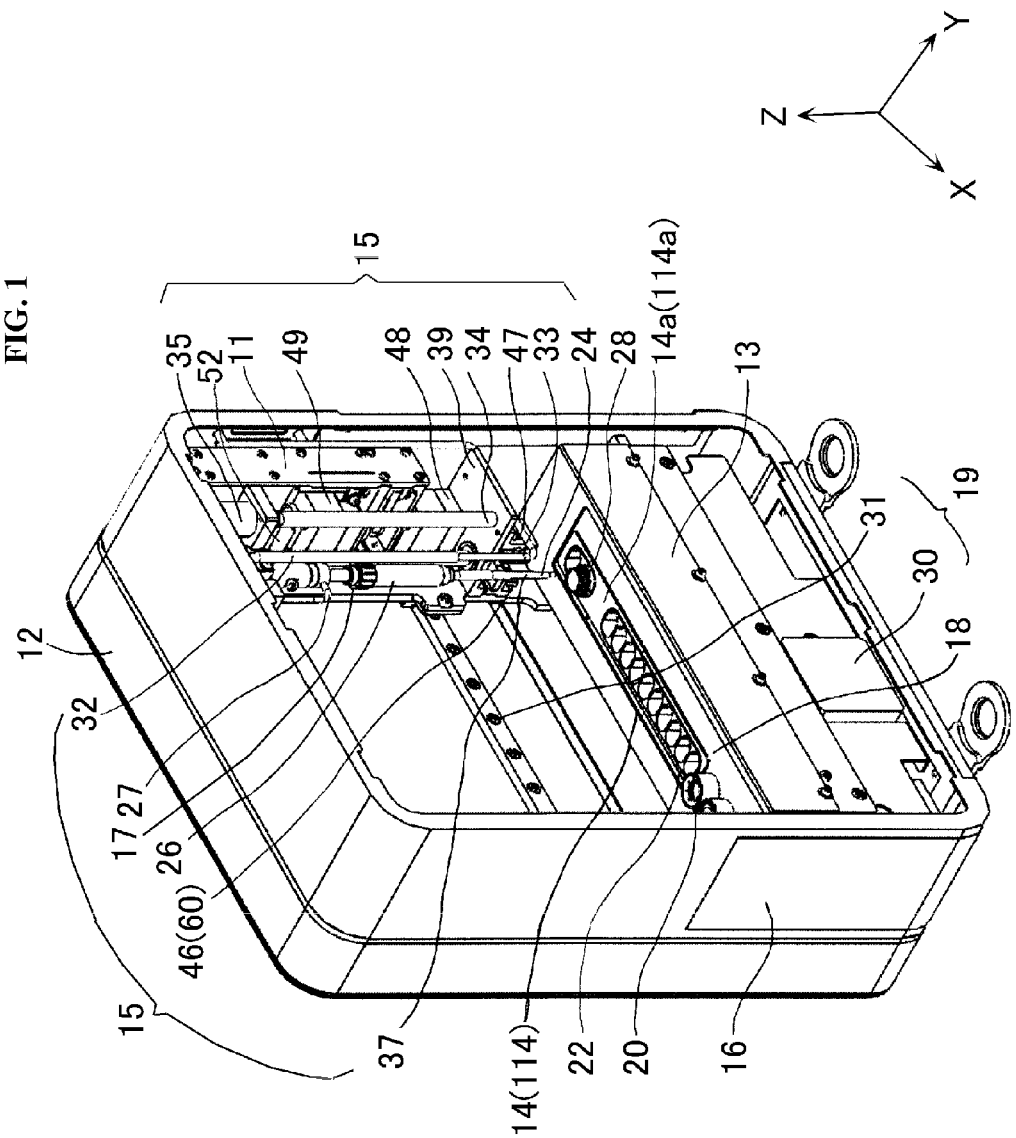
FIG. 1 is a perspective view showing a magnetic carrier treatment device according to a second embodiment that uses a magnetic reagent according to a first embodiment of the present invention.
Figure 2:
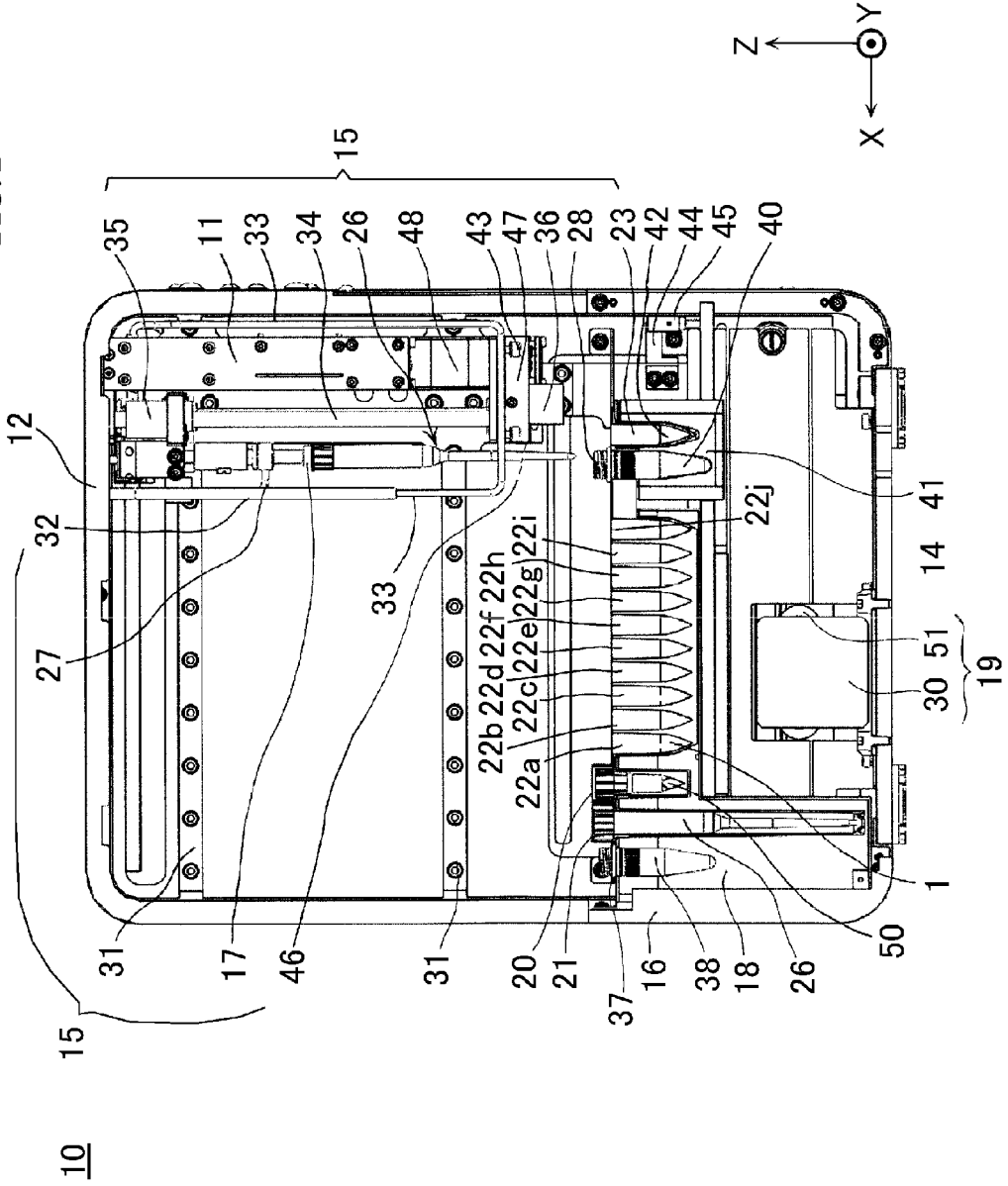
FIG. 2 is a side view of the magnetic carrier treatment device of FIG. 1.

FIG. 1 and FIG. 2 are respectively a perspective view and a side view showing a magnetic carrier treatment device 10 according to a second embodiment, that is used for loading a cartridge container 14 accommodating a magnetic reagent and a magnetic reagent kit according to a first embodiment, and treating the magnetic reagent.

The magnetic carrier treatment device 10 is surrounded by a block-shaped casing 12 of, for example, length 250 mm to 400 mm (X axis direction), width 70 mm to 100 mm (Y axis direction), and height 300 mm to 500 mm (Z axis direction). In FIG. 1, a side plate on the front side is removed to facilitate the description of the device interior. The casing 12 has: a magnetic reagent cartridge container 14 in which a suspension liquid with a magnetic reagent 1 composed of magnetic carriers 2 and treatment promoting magnetic particles 3 suspended therein is accommodated within at least one liquid accommodating part, and a plurality of (10 in this example) liquid accommodating parts 22, which accommodate or can accommodate other reagent solutions required for magnetic carrier treatment, are arranged in a single column form and are attachably and detachably provided within the casing 12; automatic treatment parts (15, 19) for performing a predetermined treatment with use of the magnetic carriers accommodated in the cartridge container 14; and a loading box 18 that has the magnetic reagent cartridge container 14 loaded therein, that is provided so as to be able to be pulled out manually to the outside from the casing 12 along with the magnetic reagent cartridge container 14, that is connected to an insertion fitting plate 16 to be inserted and fitted into a rectangular hole pierced in one side surface of the casing, and that attachably and detachably loads the magnetic reagent cartridge container 14.

The automatic treatment parts (15, 19) have a nozzle head 15 of a dispensing machine, and a movement mechanism 19 which is capable of moving the nozzle head 15 with respect to the magnetic reagent cartridge container 14 accommodated in the casing 12.

The nozzle head 15 of the dispensing machine has an X axis movement body 11 which is capable, with the movement mechanism 19, of moving with respect to the magnetic reagent cartridge container 14 accommodated in the casing 12 only in the X axis direction, which corresponds to the lengthwise direction thereof, and a cylindrical Z axis movement body 35 which is provided so as to be able to move vertically with respect to the X axis movement body 11 while being guided by a guide column 34. On the X axis movement body 11, there is screwed a nut part connected to the Z axis movement body 35, and there is rotatably attached a Z axis movement ball screw (not shown in the figure) that causes the Z axis movement body 35 to move vertically. Furthermore, on the X axis movement body 11, there are attached the guide column 34 and a supporting plate 39 attached via the guide column 34.

The nozzle head 15 has: a stainless tube 33 that is attached to the X axis movement body 11 and that is communicated with a cylinder for performing gas suction/discharging; a rubber tube 32 connected so as to have the tip end of the stainless tube 33 inserted thereinto; a nozzle 17 that is attached to the Z axis movement body 35, that is provided so that an air pipe 27 connected to the rubber tube 32 projects from the side surface thereof, and that communicates with the cylinder via the rubber tube 32; a dispensing tip 26 attachably and detachably attached to the nozzle 17; and a motor 30 that is attached to the X axis movement body 11 for driving a piston in the cylinder. Therefore, when an opening part 26a of the tip end of the dispensing tip 26 moves upward or downward in synchronization with the Z axis movement body 35, the rubber tube 32 bents or extends.

Moreover, the supporting plate 39 attached to the X axis movement body 11: supports the guide column 34; rotatably supports the ball screw; and on the lower side thereof, supports a tip attachment/detachment plate having a U-shaped cutaway part, which is larger than the diameter of the nozzle 17 and thinner than the outer diameter of the thickest portion of the tip 26, formed therein for attaching and detaching the tip such as the dispensing tip 26 from the nozzle 17, so as to be able to move in the forward/backward direction. On the upper side of the supporting plate 39, a motor 48 for driving the tip attachment/detachment plate in the forward/backward direction is supported on the supporting plate 39, that is to say, it is attached to the X axis movement body 11. The tip attachment/detachment plate is supported on a tip attachment/detachment plate supporting member 47 attached to the supporting plate 39 so as to be able to move in the forward/backward direction, and on the outer side surface of the tip attachment/detachment plate supporting member 47, there is rotatably provided a guide roller 43 which is in contact with and is guided by a guide rail provided along the X axis direction on the inner wall surface of the casing 12.

Furthermore, on the lower side of the tip attachment/detachment plate supporting member 47, a magnet 46 which moves in the forward/backward direction in synchronization with the tip attachment/detachment plate supporting member 47 is supported on a magnet supporting plate 36, and there is provided a magnetic force device 60 which is capable, with the magnet 46 moving to the close vicinity of or moving away from a small diameter tube 26b or a large diameter tube 26c of the dispensing tip 26 attached to the nozzle 17, of applying and removing a magnetic field to and from the interior of the small diameter tube or large diameter tube.

The movement mechanism 19 which moves the nozzle head 15 of the dispensing machine with respect to the magnetic reagent cartridge container 14 accommodated in the casing 12 includes: a rail 31 which cooperates with the X axis movement body 11 of the nozzle head 15 to perform guidance along the lengthwise direction of the magnetic reagent cartridge container 14, that is, the X axis direction; an X axis movement motor 30 which moves the X axis movement body of the nozzle head 15 along the X axis direction; a gear and a belt 51 which transmit rotation of the X axis movement motor 30 to the X axis movement body 11; the guide column 34 which guides the Z axis movement body 35 along the vertical direction, that is, the Z axis direction; the Z axis movement ball screw; and a Z axis movement motor 52. The cylinder and the motor 48 correspond to a suction/discharging mechanism. Moreover, the guide column 34, the Z axis movement ball screw, and the Z axis movement motor 52 correspond to a Z axis movement mechanism in the movement mechanism 19.

The loading box 18 in which the magnetic reagent cartridge container 14 is loaded, is provided so that a guide member that extends along the lengthwise direction, that is, the X axis direction of the loading box 18 can manually move in the X axis direction while being guided by the guide rail 31 provided along the X axis direction in the casing 12, and thereby, the magnetic reagent cartridge container 14 can be completely accommodated within the casing 12.

When the magnetic reagent cartridge container 14 has been loaded in the casing 12, an elastic force is applied so as to upward-bias the loading box 18 with the cartridge container 14 loaded therein, then so that the loading box 18 will not be uplifted, the cartridge container 14 is accommodated in a frame body 13 having holes that expose the opening part of the respective accommodating parts 22 and 23 of the cartridge container 14, and the cartridge container 14 is thus fixed so that it will not move.

On the end part of the loading box 18 where the insertion fitting plate 16 is provided and on the opposite end part, there is provided a positioning plate 44 for a positioning purpose that indicates that the cartridge container 14 has been loaded in a predetermined position. When a sensor 45 provided on the casing 12 side detects the positioning plate 44, it outputs a loading signal indicating that the cartridge container 14 has been loaded in the predetermined position, and when a loading signal is present, it is determined as being a state where a magnetic carrier treatment can be commenced.

As shown in FIG. 2, the magnetic reagent cartridge container 14 is a container with a single-column arrangement including: a holding hole 37 formed in a base plate 14a for attachably and detachably holding a specimen accommodating part 38 that accommodates a sample such as a specimen; a tip accommodating part 21 that has an opening part formed so as to project above the base plate 14a, and that accommodates the dispensing tip 26 so that it can be attached to the nozzle 17 as the nozzle 17 is lowered; a perforation tip accommodating part 20 that has an opening part formed so as to project above the base plate 14a, and that accommodates a perforation tip 50 formed in a tapered shape with a sharp tip end so that it can be attached to the nozzle 17 for perforating a thin membrane such as a film installed on the base plate 14a so as to cover the opening part of a liquid accommodating part 22 of the cartridge container 14; the liquid accommodating part 22 that has an opening part formed in the base plate 14a, and that accommodates or can accommodate various types of reagents including the magnetic reagent 1; a holding hole 28 that is formed in the base plate 14a in order to attachably and detachably hold a living organism accommodating part 40 that accommodates a solution produced as a result of a treatment; and a reaction container 23 that has an opening part formed in the base plate 14a, and that accommodates a solution that requires temperature control for promoting reactions. The capacity of each of the liquid accommodating parts 22, the specimen accommodating part 38, the living organism accommodating part 40, is for example, 1,000 µl, and several 100 µl of a liquid is accommodated therein to be used.

In the loading box 18 there is provided a temperature control chamber 41 having a heater that performs temperature control, and when loading the magnetic reagent cartridge container 14, the living organism accommodating part 40 and the reaction container 23 are accommodated in the temperature control chamber 41.

For example, in the case of performing a treatment for isolating a bacterial nucleic acid contained in a specimen with use of magnetic carriers, the specimen accommodating part 38 of the magnetic reagent cartridge container 14 accommodates a solution having bacteria extracted from the specimen suspended therein, and among the liquid accommodating parts 22, the liquid accommodating part 22a accommodates a magnetic reagent suspension liquid, the liquid accommodating part 22b accommodates a lysis buffer liquid that lyses the nuclei of bacteria, the liquid accommodating part 22c accommodates a neutralizing buffer liquid for adjusting the pH of the lysis buffer liquid, the liquid accommodating parts 22d to 22f accommodate various types of cleaning liquid, the liquid accommodating part 22g accommodates dissociation liquid for dissociating the nucleic acid from the magnetic carriers, and the liquid accommodating parts 22h to 22j are left empty, and the living organism accommodating part 40 and the reaction container 23 are also empty. In this state, a film type thin membrane is installed on the base plate 14a so as to cover the opening part of the liquid accommodating part 22 and the opening part of the reaction container 23.

Here, the magnetic reagent 1 is a suspension liquid containing: a plurality of magnetic carriers 2 that can be magnetized by being exposed to a magnetic field, that are coated with a material, the surface of which has an OH group, so that they can be bonded to the nucleic acid serving as a predetermined chemical substance in the liquid, and that are formed with super paramagnetic bodies of, for example, a nanosize or several 100 mm particle diameter that enables them to be suspended in the liquid; and a plurality of treatment promoting magnetic particles 3 that can be magnetized by being exposed to a magnetic field, and that are formed with iron, which is a ferromagnetic body material with a magnetic susceptibility greater than that of the magnetic carriers, and which has a particle diameter greater than that of the magnetic carriers, so that a magnetic flux greater than that of the magnetic carriers passes therethrough, with respect to the same magnetic field.

Alternatively, there may also be used a magnetic reagent cartridge container that accommodates a magnetic reagent kit, in which a suspension liquid of the magnetic carriers and a suspension liquid of the treatment promoting magnetic particles are separately accommodated in separate liquid accommodating parts 22, for example, in the liquid accommodating part 22a and in the liquid accommodating part 22b, instead of the magnetic reagent 1. In this case, the suspension liquid of the magnetic carriers and the treatment promoting magnetic particles are mixed to be used.

Figure 3:
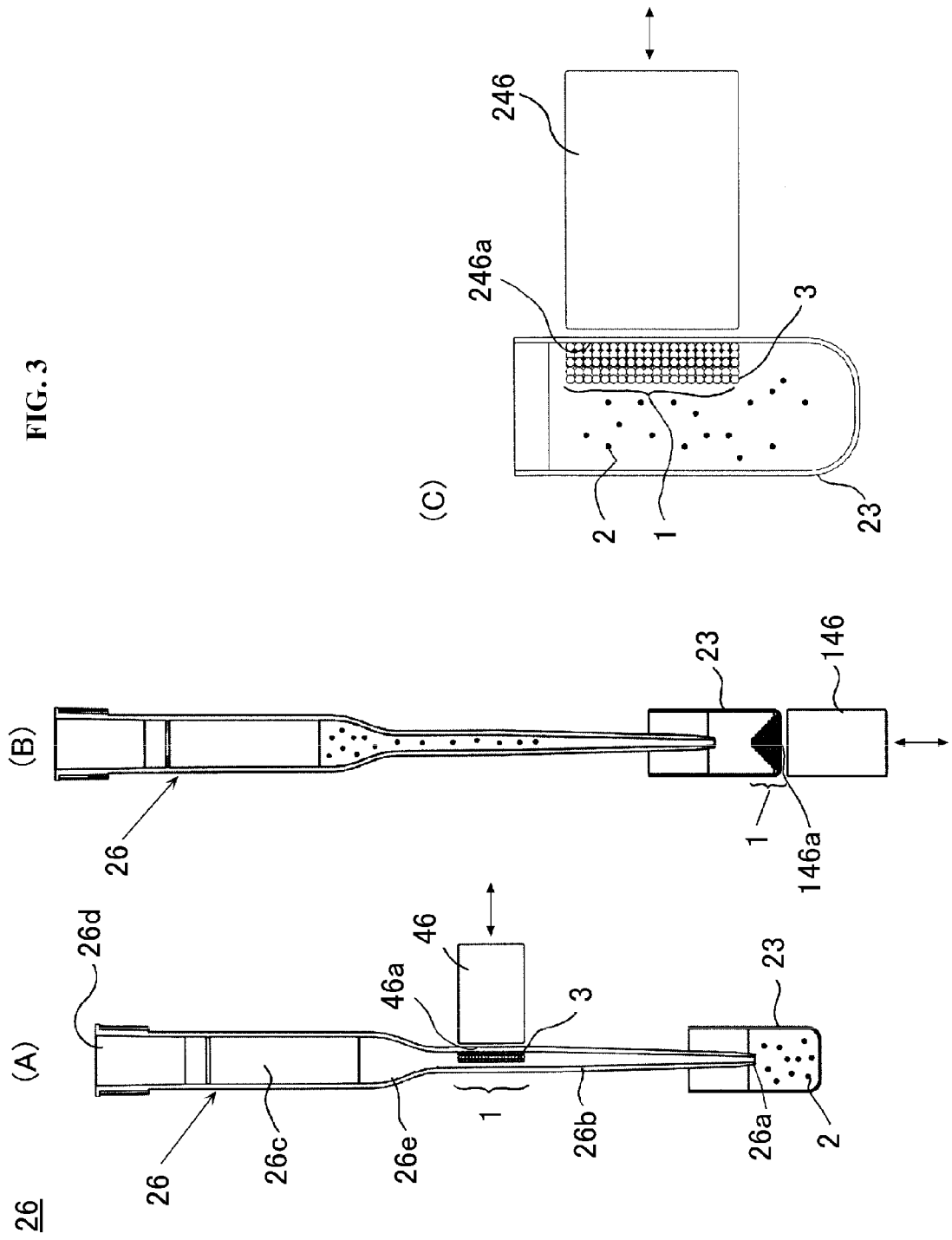
FIG. 3 is a schematic diagram showing a case of applying a magnetic field to a cartridge container of the magnetic reagent according to the first embodiment of the present invention.

FIG. 3 shows three examples of the magnetic carrier treatment device 10 according to the second embodiment, which is used loaded with the cartridge container 14 of the magnetic reagent according to the first embodiment in which is accommodated a liquid suspending the magnetic reagent 1.

FIG. 3 (A) shows a first example of the magnetic carrier treatment device 10 according to the second embodiment, and it shows: a dispensing tip 26 having a small diameter tube 26b with an opening part 26a on the tip end thereof, a large diameter tube 26c of a diameter greater than that of the small diameter tube 26b with an attachment opening part 26d that can be attached to the nozzle 17, and a transition part 26e that connects the small diameter tube 26b and the large diameter tube 26c; a magnet 46 that is provided so as to be able to move toward and move away from the small diameter tube 26b of the dispensing tip 26; and a reaction container 23 of the cartridge container 14 that is provided so as to be able to have the opening part 26a of the small diameter tube 26b inserted thereinto. The dispensing tip 26 is, for example, such that the inner diameter of the small diameter tube 26b is approximately 1 mm to 3 mm, the inner diameter of the large diameter tube 26c is approximately 8 mm to 9 mm, and the lengthwise length thereof is approximately 100 mm. The inner wall portion of the small diameter tube 26b, toward which the magnet 46 moves, corresponds to a capturing region 46a. In FIG. 3 (A), the dispensing tip 26 repeatedly suctions and discharges a target containing solution accommodated in the reaction container 23 and added with the magnetic reagent 1 having magnetic carriers 2 capable of bonding the target, in a state where the magnet 46 is brought to the vicinity thereof, and thereby, the nanosized magnetic carriers 2 bonded to the target are adsorbed on the inner wall of the small diameter tube 26b and on treatment promoting magnetic particles 3, using the magnetic force strengthened by the treatment promoting magnetic particles 3. The magnitude of the magnetic field of the magnet 46 is, for example, 1,000 gauss to several thousands gauss.

FIG. 3 (B) shows a second example of the magnetic carrier treatment device 10 according to the second embodiment, wherein instead of providing the magnet 46 of the magnetic carrier treatment device 10 according to the first example so as to be capable of moving toward and away from the dispensing tip 26, on the lower side of the cartridge container 14, there is provided a magnet 146 capable of moving toward and away from the bottom of the reaction container 23 of the cartridge container 14. After having agitated a solution that contains a target capable of bonding to magnetic carriers 2 contained in the magnetic reagent 1, dispensed with the dispensing tip 26 into the reaction container 23 accommodating the magnetic reagent 1, a magnetic field is applied to the interior of the reaction container 23 by bringing the magnet 146 to the vicinity of the bottom of the reaction container 23, and with use of the treatment promoting magnetic particles 3, the magnetic carriers 2 bonded to the target are adsorbed and deposited on the bottom of the reaction container 23 or are adsorbed on the treatment promoting magnetic particles 3 adsorbed and deposited on the inner bottom, to thereby separate them. This inner bottom corresponds to the capturing region 146a.

FIG. 3 (C) shows a third example of the magnetic carrier treatment device 10 according to the second embodiment, and it shows an example where instead of the magnet 46 of the magnetic carrier treatment device 10 according to the first example, a magnet 246 is provided on the side surface of the reaction container 23 of the cartridge container 14 that accommodates the magnetic reagent 1 so as to be able to move toward and away from the reaction container 23. By bringing the magnet 246 to the vicinity of the reaction container 23 that accommodates the magnetic reagent 1, a magnetic field is applied to the interior of the reaction container 23, and with use of the magnetic carriers 2 bonded to the target and the treatment promoting magnetic particles 3, the magnetic reagent 1 is adsorbed on the inner side surface of the reaction container 23. In this case, the inner side surface corresponds to the capturing region 246a. The magnet is provided so as to be able to move toward and away from the side surface or the bottom surface of another liquid accommodating part of the cartridge container 14 instead of the reaction container 23.

Figure 4:
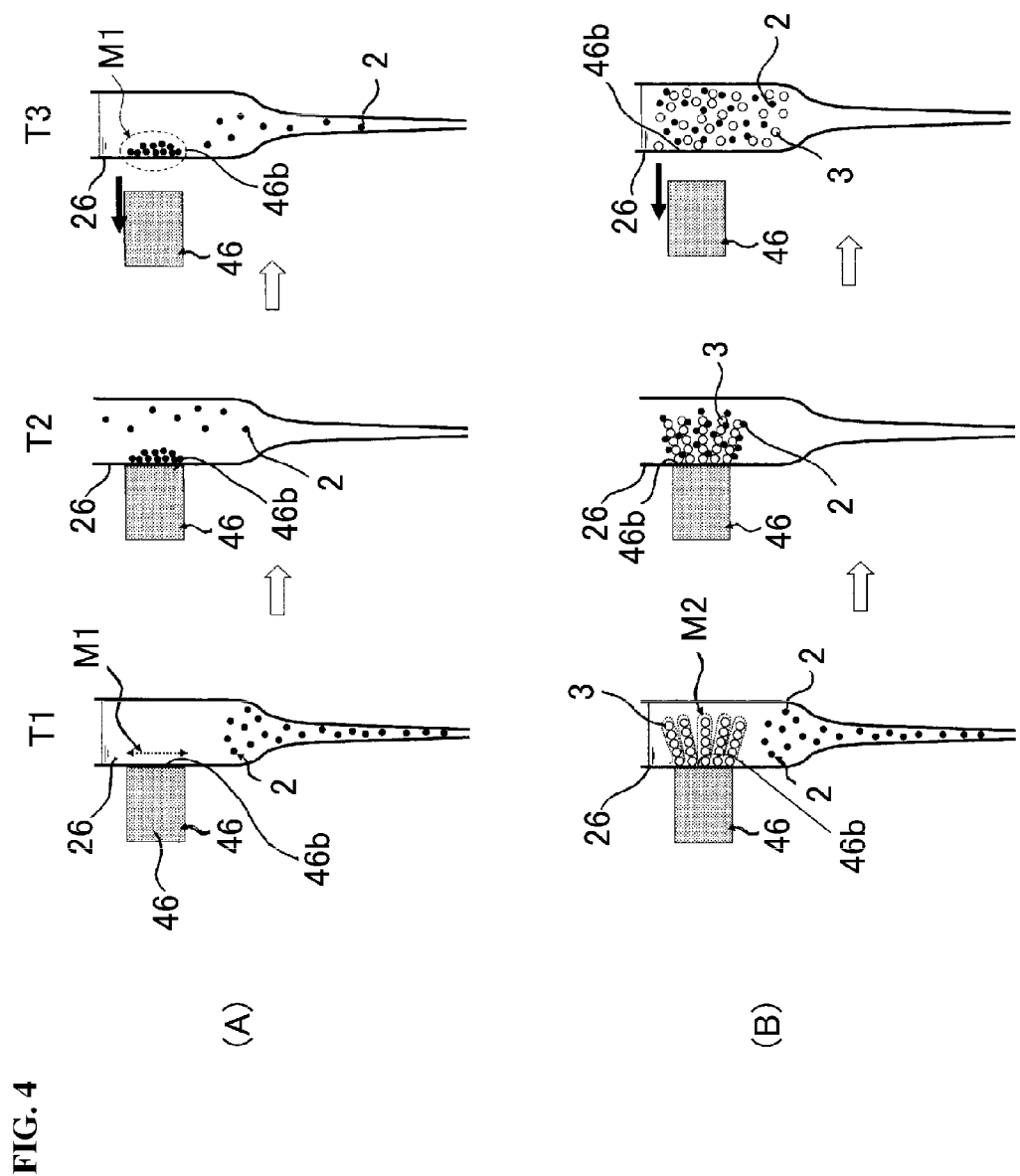
FIG. 4 is a contrast diagram of a case of using the magnetic reagent according to the first embodiment of the present invention.

FIG. 4 is a schematic diagram regarding the first magnetic reagent 1 showing, with a time-line (T1, T2, and T3), changes in the state of the magnetic field in the case where a liquid (A) with only magnetic carriers 2 suspended therein and a liquid (B) with magnetic carriers 2 and treatment promoting magnetic particles 3 suspended therein are suctioned into the dispensing tip 26, and the magnet 46 is brought to the vicinity of the large diameter tube thereof to thereby apply and remove a magnetic field to and from the interior of the large diameter tube.

At time T1, there is shown a capturing region 46b where the magnetic carriers 2 are directly adsorbed in the case where the magnet 46 is brought to the vicinity of the large diameter tube 26c of the dispensing tip 26 when suctioning the suspension liquid into the dispensing tip, and M1 and M2 each represent an effective magnetic field reaching range (area) based on the capturing region 46b. The (A) side shows the case of suctioning the liquid with only the magnetic carriers 2 suspended therein into the dispensing tip 26, where the magnetic carriers 2 have not been adsorbed on the capturing region 46b. This shows that the effective magnetic field reaching range M1 corresponds to the capturing region 46b. On the other hand, the (B) side shows the case of suctioning the liquid with the magnetic carriers 2 and the treatment promoting magnetic particles 3 suspended therein, showing a state where the treatment promoting magnetic particles 3 that receive and create a greater magnetic force than the magnetic carriers 2 are adsorbed directly on the capturing region 46b, or they are indirectly adsorbed via other treatment promoting magnetic particles 3, and the treatment promoting magnetic particles 3 are chain-connected along the magnetic force lines. This shows that due to this, the capturing region 46b where the magnetic carriers 2 can be directly adsorbed has expanded to the effective magnetic field reaching range (area) M2 including the surface area of the treatment promoting magnetic particles 3. Therefore, it is shown that M2 is significantly greater than M2.

The step at time T2 shows a state where suction/discharging have been performed several times and suction is being performed in each dispensing tip 26 while the magnet is staying in the vicinity. The (A) side shows that since the liquid only has the magnetic carriers 2 suspended therein, although part of the magnetic carriers 2 that have passed through the effective magnetic field reaching range M1 are directly or indirectly adsorbed on the capturing region 46b, the effective magnetic field reaching range M1 of the capturing region 46b is merely the vicinity of the inner wall on the side to which the magnet 46 has approached, and therefore, the magnetic carriers 2 present in the majority of locations distanced therefrom have not been captured and are in the state of being suspended. On the other hand, on the (B) side, since the liquid has the magnetic carriers 2 and the treatment promoting magnetic particles 3 suspended therein, the magnetic carriers 2 that have passed through the effective magnetic field reaching range M2 are directly or indirectly adsorbed on the capturing region 46b, and the effective magnetic field reaching range based on the capturing region 46b has expanded to M2. Therefore, the magnetic carriers 2 that are present in locations distanced from the inner wall on the side to which the magnet 46 has approached, are also captured.

The step at time T3 shows a state where the magnet 46 has moved away from the large diameter tube of the dispensing tip 26, suction/discharging have been performed several times within the dispensing tip 26, and suction is being performed. On the (A) side, since the captured magnetic carriers 2 are tightly attached to each other, the magnetic carriers 2 are still being captured on the capturing region 46b or the effective magnetic field reaching range M1 in a pellet-like state even when suction/discharging are repeated, and only the magnetic carriers 2 that have not been captured are suspended. On the other hand, on the (B) side, when suction/discharging are repeated after the magnetic field in the large diameter tube has been removed, the treatment promoting magnetic particles 3 are influenced by the movement of the liquid and are likely to be dispersed or suspended more than the magnetic carriers 2, and the magnetic carriers 2 are not tightly attached to each other and adsorbed on the treatment promoting magnetic particles 3. As a result, they are likely to dissociate or depart, and the magnetic carriers 2 are re-suspended in a short period of time.

Figure 5:
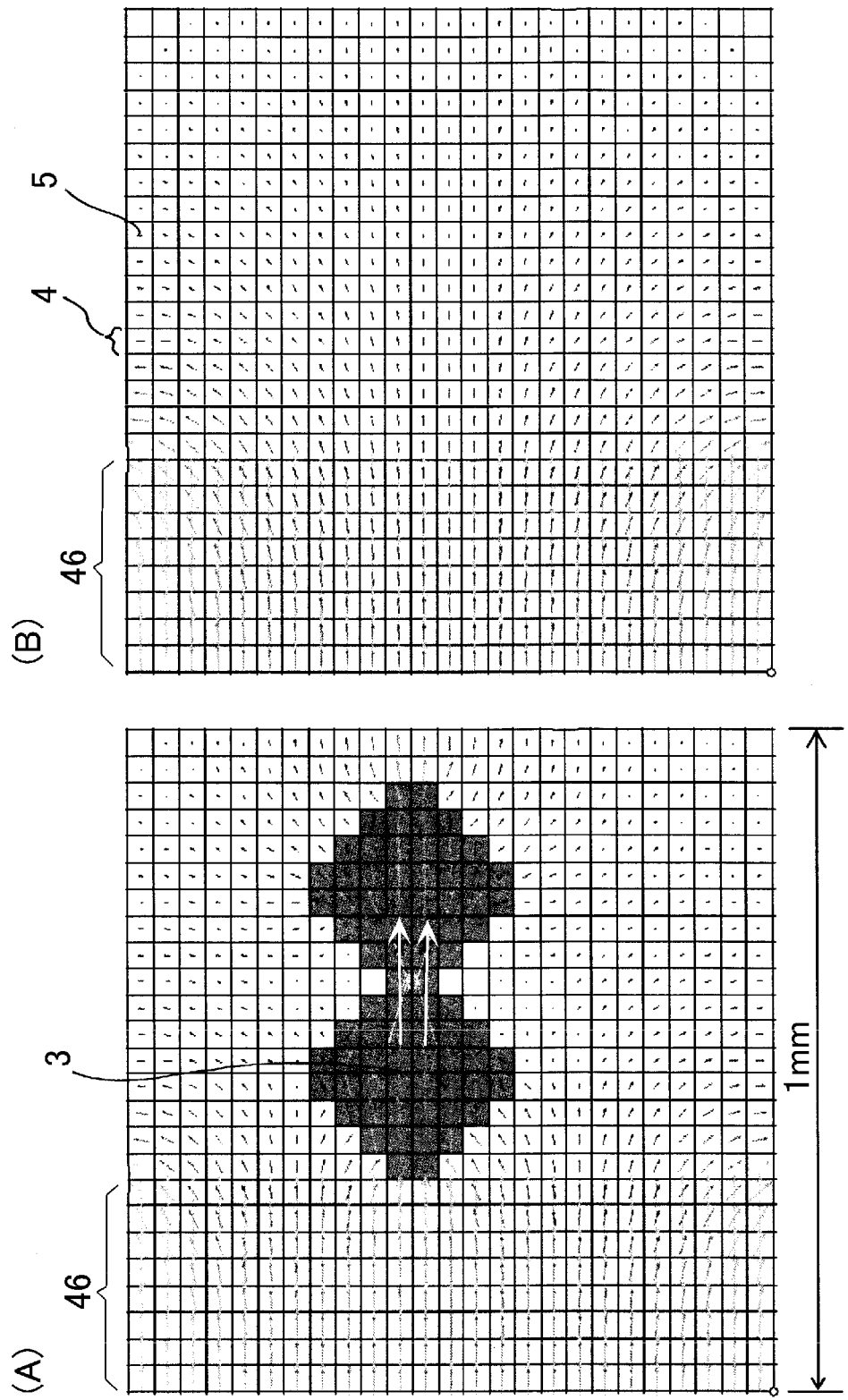
FIG. 5 is a state diagram showing a state of a magnetic field in a case where treatment promoting magnetic particles of the present invention are present.

Next, FIG. 5 shows, with a simulation, that the presence of treatment promoting magnetic particles 3 of the magnetic reagent 1 strengthened the magnetic field (magnetic flux density) at the periphery thereof.

In this simulation, it is assumed that in a two dimensional space of 1 mm height and width, a two dimensional magnet model (46) imitating a magnet 46 of 1 mm height and 0.32 mm width with 1 gauss magnetic flux density is placed on the left side of the diagram of the two dimensional space, and iron powder with a magnetic permeability 1,000 times that of water is stationarily placed in each square 4 (0.04 mm height and 0.04 mm width) of the magnet model (46). Each arrow 5 shows the vector of the magnetic flux density obtained in the simulation at the position where the iron powder is placed.

Here, FIG. 5 (A) shows, in the case where two dimensional particle models (3) imitating two treatment promoting magnetic particles 3 of a particle diameter 0.32 mm are chain-connected along the normal line with respect to the magnet model (46) and are adsorbed on the magnet model (46), the magnetic flux density vector is exerted in the particle model (3) and on each iron powder, and FIG. 5 (B) shows the magnetic flux vector exerted on each iron powder when the particle model (3) is not present. Comparing these two diagrams, it can be understood that the presence of the treatment promoting magnetic particles 3 strengthens the magnetic field (magnetic flux density) even at the location sufficiently distanced from the magnet 46, compared to the case where the treatment promoting magnetic particles 3 are not present.

Figure 6:
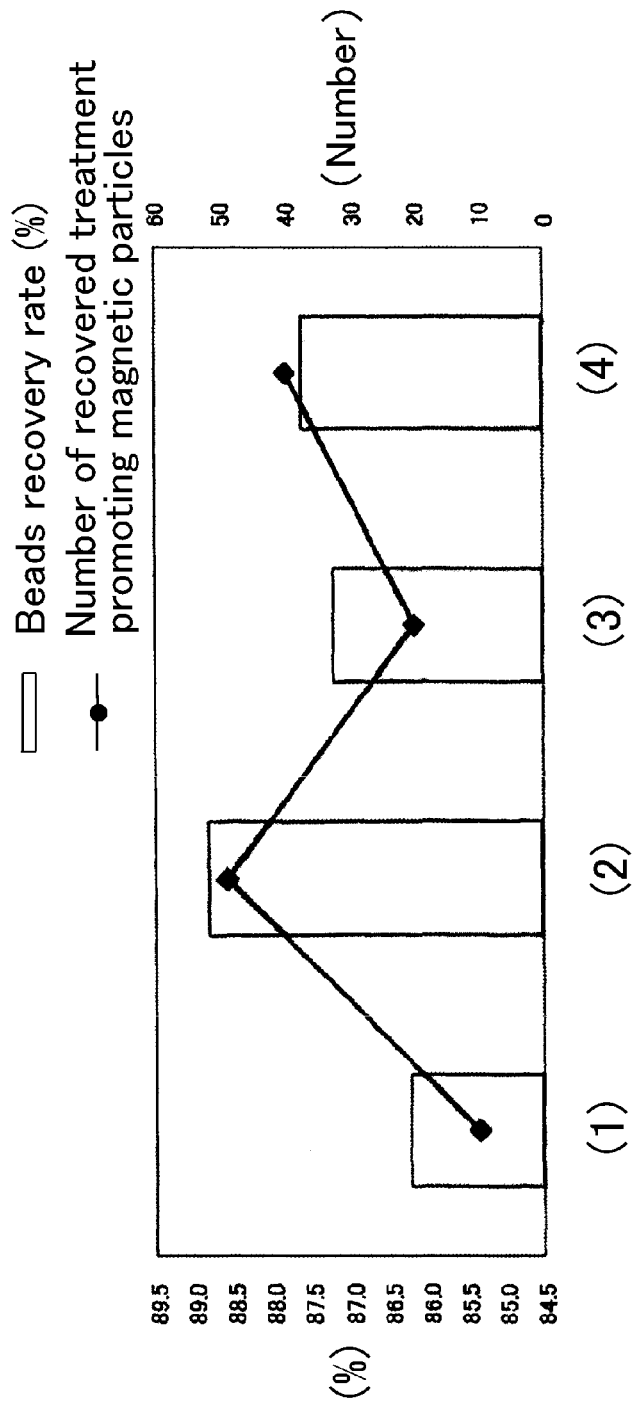
FIG. 6 is a bar/sequential line graph showing magnetic carrier recovery rates prior to a dispersion treatment according to the first embodiment of the present invention.
Figure 7:
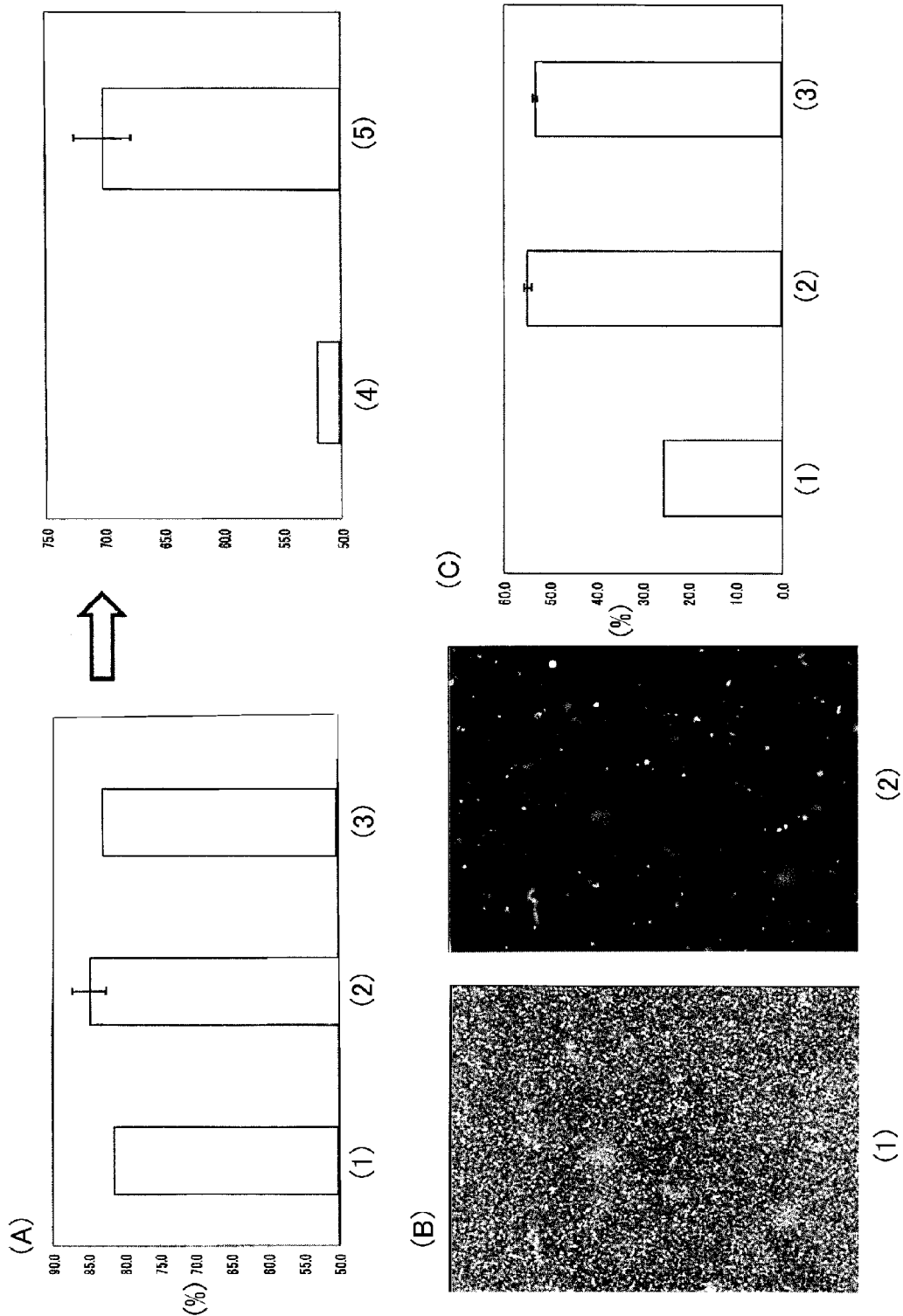
FIG. 7 includes bar charts showing magnetic carrier recovery rates before and after the dispersion treatment, and photographs showing experiment results of the dispersion treatment according to the first embodiment of the present invention.

FIG. 6 and FIG. 7 are graphs and photographs showing experiment results to illustrate that the presence of treatment promoting magnetic particles improves the recovery rate of magnetic carriers.

In this experiment, there was used a suspension liquid that contained, as magnetic carriers, nanosized magnetic carriers for capturing nucleic acid formed with iron oxide, however, there was a possibility that the magnetic carriers may be agglutinated in the suspension liquid. Accordingly, measurements were made respectively in the case of using magnetic carriers prior to a dispersion treatment, and the case of using the magnetic carriers after they have been dispersion-treated. Here, the dispersion treatment was performed by means of centrifugal separation.

As the treatment promoting magnetic particles to be contained in the magnetic reagent used, any one of the following four types of treatment promoting magnetic particles was used. That is to say, the first treatment promoting magnetic particles were product name "Steel Shot", code name "TSH30" (product of IKK SHOT Co, Ltd.), of a particle diameter 425-125 μm, containing components within iron namely carbon 0.8-1.2%, silicon not less than 0.4%, manganese not less than 0.35% and not more than 1.0%, phosphorus not more than 0.05%, and sulfur not more than 0.05%. The second treatment promoting magnetic particles were product name "Steel Shot", code name "TSH60" (product of IKK SHOT Co, Ltd.), of a particle diameter 850-355 μm, which differed from that of the first treatment promoting magnetic particles. The third treatment promoting magnetic particles were product name "Steel Beads", code name "SB50" (product of Fuji Manufacturing Co., Ltd.), of a particle diameter 425-125 μm, containing components within iron namely carbon 0.9-1.1%, silicon not less than 1.3%, manganese not more than 1.0%, phosphorus not more than 0.05%, and sulfur not more than 0.05%. The fourth treatment promoting magnetic particles were product name "PSS Beads" (product of Precision System Science Co., Ltd.) of a particle diameter 0.5 μM to 2 μm, and they were amorphous nucleic acid refined particles of a particle diameter 190 nm, coated with a material having an OH group on the $Fe_3O_4$ surface.

Having prepared 10 of the magnetic reagent cartridge containers 14, the liquid accommodating part 22a of the first magnetic reagent cartridge 14 accommodated 500 μl of a first magnetic reagent having a magnetic carrier suspension liquid prior to a dispersion treatment and 20 of the first treatment promoting magnetic particles suspended therein, and the liquid accommodating part 22b accommodated 500 μl of a cleaning liquid (for example, distilled water). Similarly, the liquid accommodating part 22a of the second magnetic reagent cartridge container 14 accommodated a second magnetic reagent having the magnetic carrier suspension liquid prior to a dispersion treatment and 50 of the first treatment promoting magnetic particles suspended therein, the liquid accommodating part 22b similarly accommodated 500 μl of the cleaning liquid, the liquid accommodating part 22a of the third magnetic reagent cartridge container 14 accommodated 500 μl of a third magnetic reagent having the magnetic carrier suspension liquid prior to the dispersion treatment and 20 of the third treatment promoting magnetic particles suspended therein, and the liquid accommodating part 22b similarly accommodated the cleaning liquid. The liquid accommodating part 22a paired with the fourth magnetic reagent cartridge container 14 accommodated 500 μl of a fourth magnetic reagent having the magnetic carrier suspension liquid prior to the dispersion treatment and 50 of the third treatment promoting magnetic particles suspended therein, and the liquid accommodating part 22b similarly accommodated the cleaning liquid.

The liquid accommodating part 22a of the fifth magnetic reagent cartridge container 14 accommodated only 500 μl of the magnetic carriers prior to the dispersion treatment, and the liquid accommodating part 22b similarly accommodated the cleaning liquid. The liquid accommodating part of the sixth magnetic reagent cartridge container 14 accommodated 500 μl of a fifth magnetic reagent having the magnetic carrier suspension liquid prior to the dispersion treatment, 20 of the third treatment promoting magnetic particles, and 1 second treatment promoting magnetic particle suspended therein, and the liquid accommodating part 22b similarly accommodated the cleaning liquid. The liquid accommodating part 22a of the seventh magnetic reagent cartridge container 14 accommodated 500 μl of a sixth magnetic reagent having the magnetic carrier suspension liquid prior to the dispersion treatment and 30 μl of the fourth treatment promoting magnetic particles suspended therein, and the liquid accommodating part 22b similarly accommodated the cleaning liquid.

The liquid accommodating part 22a of the eighth magnetic reagent cartridge container 14 accommodated 500 μl of the magnetic carriers prior to the dispersion treatment, and the liquid accommodating part 22b similarly accommodated the cleaning liquid. The liquid accommodating part 22a of the ninth magnetic reagent cartridge container 14 accommodated 500 μl of a seventh magnetic reagent having the magnetic carrier suspension liquid prior to the dispersion treatment, 20 of the third treatment promoting magnetic particles, and 1 second treatment promoting magnetic particle suspended therein, and the liquid accommodating part 22b similarly accommodated the cleaning liquid. The liquid accommodating part 22a of the tenth magnetic reagent cartridge container 14 accommodated 500 μl of an eighth magnetic reagent having the magnetic carrier suspension liquid prior to the dispersion treatment and 30 μl of the fourth treatment promoting magnetic particles, and the liquid accommodating part 22b similarly accommodated the cleaning liquid.

Then, the first magnetic reagent cartridge container 14 was loaded in the magnetic carrier treatment device 10; when inserting the tip end of the dispensing tip 26 into the liquid accommodating part 22a and suctioning the suspension liquid using the dispensing tip 26, by bringing the magnet 46 to the vicinity of the small diameter tube 26b and applying a magnetic field to the interior of the small diameter tube 26b, the magnetic carriers and the first treatment promoting magnetic particles of the first magnetic reagent were adsorbed on the inner wall of the small diameter tube 26b of the dispensing tip 26; while they were being adsorbed, the dispensing tip 26 was raised in the Z axis direction and the dispensing tip 26 was removed from the liquid accommodating part 22a; by moving the nozzle head 15 along the cartridge container 14, the dispensing tip 26 was moved to the position of the liquid accommodating part 22b and the tip end of the dispensing tip 26 was inserted into the liquid accommodating part 22b; by repeatedly suction/discharging the cleaning liquid in the state where the magnet 46 was in the vicinity of the small diameter tube 26b, the magnetic carriers and the first treatment promoting magnetic particles were cleaned; and then the magnet 46 was moved away from the small diameter tube 26b to remove the magnetic field from the interior of the small diameter tube 26b, and suction/discharging were repeated, to thereby achieve suspension in the liquid.

Accordingly the residual liquid in the liquid accommodating part 22a was measured on an absorption spectrometer of 480 nm, to thereby calculate the recovery rate of the magnetic carriers.

As a result, as shown by (1) in the bar/sequential line graph of FIG. 6, the recovery rate of the magnetic carriers that may have been agglutinated before the dispersion treatment was approximately 86.3%, and the number of recovered first treatment promoting magnetic particles was found to be 10.

Similarly, regarding the second magnetic reagent cartridge container 14 in which the number of the first treatment promoting magnetic particles was increased to 50, as shown by (2) of the bar/sequential line graph in FIG. 6, the recovery rate of the magnetic carriers increased and was found to be approximately 89.0%, and the number of the recovered first treatment promoting magnetic particles was found to be approximately 50.

Similarly, the case of using the third magnetic reagent cartridge container 14 is shown by (3) of the bar/sequential line graph in FIG. 6, and the case of using the fourth magnetic reagent cartridge container 14 is shown by (4) of the bar/sequential line graph in FIG. 6, indicating that the increase in the number of treatment promoting magnetic particles contributes to improve the recovery rate of magnetic carriers.

Moreover, in the case where the fifth magnetic reagent cartridge container 14 was used with the magnetic carriers prior to the dispersion treatment and no treatment promoting magnetic particles were present, as shown by (1) of the bar graph in FIG. 7(A), the recovery rate thereof was approximately 82%, and in the case with the magnetic carriers prior to the dispersion treatment where the treatment promoting magnetic particles were present, as shown by (2) of the bar graph of FIG. 7 (A), the recovery rate was rising compared to the case where the treatment promoting magnetic particles were not present. Similarly, (3) of the bar graph of FIG. 7 (A) shows the case of using the seventh magnetic reagent cartridge container 14. At this time, in the case where the flow rate of the liquid suction/discharging of the nozzle was increased by four times (the pulse number of the stepping motor was increased from 62 to 262), as shown by (4) of the bar graph of FIG. 7 (A), the recovery rate was lower than that in the case where the treatment promoting magnetic particles were not present as shown in FIG. 7 (A) (1). This is because the level of responsiveness of the magnetic carriers with respect to the magnetic field is low, and therefore, an increase in the flow rates of suction/discharging influences the recovery rate. On the other hand, in the case where the sixth cartridge container 14 was used with magnetic carriers prior to the dispersion treatment and the treatment promoting magnetic particles were present, as shown by (5) of the bar graph of FIG. 7 (A), the recovery rate was not very much lower than that in the case of having no treatment promoting magnetic particles shown in FIG. 7 (A) (2) although the flow rate increased by four times. Therefore, in the case of using the treatment promoting magnetic particles, the treatment that required approximately 20 minutes when they were not present can be performed in approximately 5 minutes without compromising recovery rate very much, and the speed of the treatment can be increased.

The photo (1) of FIG. 7 (B) is an observation of the suspension liquid used for the magnetic carriers prior to the dispersion treatment, made by a microscope of 400 times enlargement, and the photo (2) of FIG. 7 (B) is an observation of the supernatant liquid produced as a result of 2,000 G centrifugal separation performed on the suspension liquid prior to the dispersion treatment, made by a microscope of 400 times enlargement. The photo shows that the number of the particles decreased although large particles are still observed in the supernatant liquid, and the orange color of the liquid indicates that the suspended magnetic carriers have a nanosized particle diameter.

(1) of the bar graph of FIG. 7 (C) shows the case of using the eighth magnetic reagent cartridge container 14, illustrating the case where the suspension liquid of the magnetic carriers after the dispersion treatment was used and treatment promoting magnetic particles were not present, and the recovery rate thereof was less than 30%. (2) of the bar graph of FIG. 7 (C) shows the case of using the ninth magnetic reagent cartridge container 14, illustrating the case where 500 μl of the seventh magnetic reagent containing the magnetic carriers after the dispersion treatment was used, and the recovery rate of the magnetic carriers exceeded 50%. (3) of the bar graph of FIG. 7 (C) shows the case of using the tenth magnetic reagent cartridge container 14, illustrating the case where 500 μl of the eighth magnetic reagent containing the magnetic carriers after the dispersion treatment was used, and the recovery rate of these magnetic carriers also exceeded 50%.

That is to say, given that a dispersion treatment is normally required when using magnetic carriers for a treatment, in the case of using these treatment promoting magnetic particles, compared to the case of not using them, twice or more the recovery rate of the magnetic carriers has been obtained in this example, indicating that the recovery rate of magnetic carriers can be significantly increased with treatment promoting magnetic particles.

Figure 8:
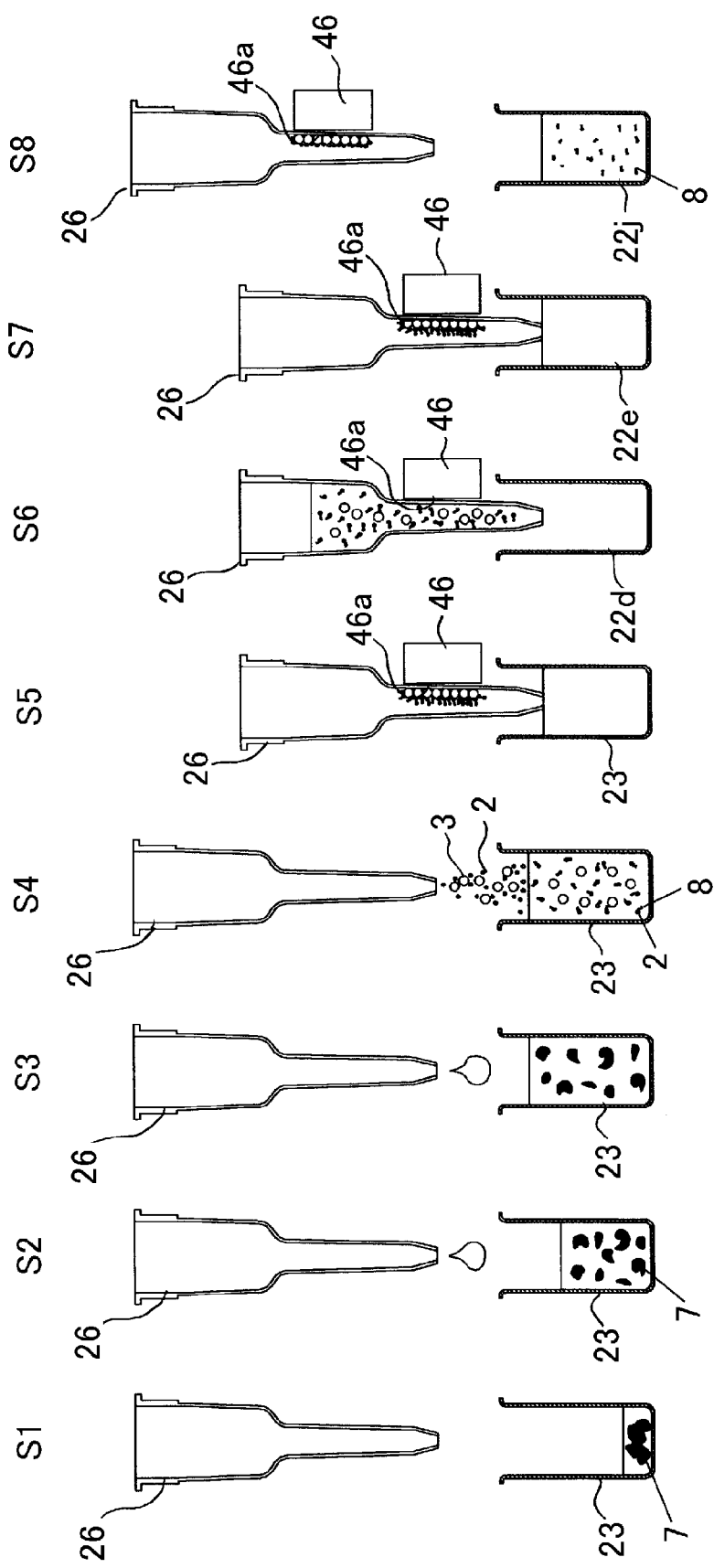
FIG. 8 is a flow diagram of a case of using the magnetic carrier treatment device according to the second embodiment of the present invention.

FIG. 8 shows a flow chart of a magnetic carrier capturing treatment with use of the cartridge container 14 for the magnetic reagent according to the first embodiment and the above device 10 according to the second embodiment.

For example, the specimen accommodating part 38 of the cartridge container 14 accommodates a sample solution containing bacteria 7 preliminarily extracted from a patient as a sample. The liquid accommodating part 22a pre-accommodates a suspension liquid of a magnetic reagent containing magnetic carriers 2 of super paramagnetic bodies of a nanosized particle diameter and treatment promoting magnetic particles 3 of, for example, several tens of μm particle diameter formed with ferromagnetic bodies. Moreover, the liquid accommodating part 22b accommodates a lysis buffer liquid for lysing the bacteria, the liquid accommodating part 22c accommodates a neutralizing buffer liquid, the liquid accommodating part 22d through the liquid accommodating part 22i accommodate various types of cleaning liquid, and the liquid accommodating part 22j accommodates the eluate.

In step S1, the nozzle head 15 is moved in the positive direction of the X axis, and the nozzle 17 is positioned above the dispensing tip 26 held on the tip accommodating part 21 of the cartridge container 14. Next, the Z axis movement body 35 is lowered so that the nozzle head 15 is inserted, fitted, and attached into the attachment opening part 26d of the dispensing tip 26, and then, it is raised and the tip end of the dispensing tip 26 is positioned above the base plate 14a of the cartridge container 14.

Next, the nozzle head 15 is further moved in the positive direction of the X axis to above the specimen accommodating part 38, and the Z axis movement body 35 is lowered to thereby insert the tip end of the dispensing tip 26 into the specimen accommodating part 38. Then, part of the sample solution containing the bacteria is suctioned, and having raised the tip end of the dispensing tip 26, it is positioned above the base plate 14a of the cartridge container 14. Next, the nozzle head 15 is moved along the negative direction of the X axis, to thereby position it above the reaction container 23. By lowering the Z axis movement body 35, the sample liquid is discharged into the reaction container 23.

In step S2, the nozzle head 15 is moved along the positive direction of the X axis to position it above the liquid accommodating part 22b, and it is then lowered along the Z axis to insert the tip end of the dispensing tip 26 into the liquid accommodating part 22b, to thereby suction the lysis buffer liquid accommodated in the liquid accommodating part 22b.

Having completed the suction, the dispensing tip 26 is raised in the Z axis direction and positioned above the base plate 14a of the cartridge container 14, and it is then moved in the negative direction of X axis, to thereby position it above the reaction container 23. The dispensing tip 26 is lowered to insert the tip end of the dispensing tip 26 into the reaction container 23, and the lysis buffer liquid is discharged into the reaction container 23. By repeatedly performing suction/discharging using the dispensing tip 26, the lysis buffer liquid and the sample liquid are agitated. Incubation is performed for a predetermined period of time. As a result, the suspended bacteria and nuclei of the bacteria are destroyed, and nucleic acid lyses into the liquid containing the lysis buffer liquid.

In step S3, the nozzle head 15 is moved along the positive direction of the X axis to position it above the liquid accommodating part 22c, and it is then lowered along the Z axis to insert the tip end of the dispensing tip 26 into the liquid accommodating part 22c, to thereby suction the neutralizing buffer liquid.

Having completed the suction, the dispensing tip 26 is raised in the Z axis direction and positioned above the base plate 14a of the cartridge container 14, and it is then moved in the negative direction of X axis, to thereby position it above the reaction container 23. The dispensing tip 26 is lowered to insert the tip end of the dispensing tip 26 into the reaction container 23, and the neutralizing buffer liquid is discharged into the reaction container 23. By repeatedly performing suction/discharging using the dispensing tip 26, the neutralizing buffer liquid is agitated with the liquid accommodated in the reaction container 23, to thereby cause it to react with the lysis buffer liquid to neutralize it.

In step S4, the nozzle head 15 is moved in the positive direction of the X axis to position it above the liquid accommodating part 22a, and then, it is lowered along the Z axis to insert the tip end of the dispensing tip 26 into the liquid accommodating part 22a for suctioning the suspension liquid serving as the magnetic reagent 1 containing the magnetic carriers 2 and the treatment promoting magnetic particles 3.

Next, the dispensing tip 26 is raised in the Z axis direction and positioned above the base plate 14a of the cartridge container 14, and after having moved the nozzle head 15 in the negative direction of the X axis and positioned it above the reaction container 23, it is lowered in the Z axis direction and the suspension liquid containing the magnetic carriers 2 and the treatment promoting magnetic particles 3 is discharged into the reaction container 23. The suspension liquid, in which the magnetic carriers 2 and the treatment promoting magnetic particles 3 are suspended or dispersed in the solution of the nucleic acid 8 accommodated in the reaction container 23, is suctioned and discharged repeatedly using the dispensing tip 26 to thereby agitate it, and the magnetic carriers 2 and the nucleic acid 8 are made to encounter with each other to thereby bond the nucleic acid 8 to the magnetic carriers 2.

In step S5, by applying a magnetic field to the interior of the small diameter tube 26b when suctioning the suspension liquid in a state where the magnet 46 is in the vicinity of the small diameter tube 26b of the dispensing tip 26, the magnetic carriers 2 bonded to the nucleic acid 8 and the treatment promoting magnetic particles 3 in the suspension liquid are magnetized. As a result, since the particle diameter and the magnetic susceptibility of the treatment promoting magnetic particles 3 dispersed or suspended in the suspension liquid are greater than those of the magnetic carriers 2, the treatment promoting magnetic particles 3 are directly or indirectly attracted to the capturing region 46a, which is the inner wall of the dispensing tip 26 on the side, to which the magnet 46 has approached, by a magnetic force greater than that for the magnetic carriers 2, while attracting or adsorbing the magnetic carriers 2 suspended at the periphery thereof. In this state, by repeatedly performing suction/discharging, the magnetic carriers 2 in the suspension liquid can be efficiently captured on the inner wall.

In step S6, in the state where the magnetic carriers 2 and the treatment promoting magnetic particles 3 are captured on the inner wall of the small diameter tube of the dispensing tip 26 while the magnetic 46 is in the vicinity of the small diameter tube (26b) of the dispensing tip 26, the dispensing tip 26 is raised along the Z axis to extract it from the reaction container 23 and position it above the cartridge container 14. The dispensing tip 26 is moved in the positive direction along the X axis while having the magnetic carriers 2 and the treatment promoting magnetic particles 3 captured thereinside, to thereby position it above the liquid accommodating part 22d. In the state where the magnet 46 is in the vicinity of the small diameter tube of the dispensing tip 26, the dispensing tip 26 is lowered along the Z axis to insert the tip end of the dispensing tip 26 into the liquid accommodating part 22d. Then, in the state where the magnet 46 is moved away and the magnetic field is removed, the cleaning liquid accommodated in the liquid accommodating part 22d is suctioned/discharged, to thereby clean the magnetic carriers 2 and the treatment promoting magnetic particles 3.

If necessary, in step S7, the dispensing tip 26 is further moved to the liquid accommodating part 22e to thereby perform further cleaning. When the cleaning is completed, in the state where the magnet 46 is in the vicinity of the small diameter tube of the dispensing tip 26, suction/discharging are repeatedly performed to thereby capture the magnetic carriers 2 and the treatment promoting magnetic particles 3. While the magnetic carriers 2 and the treatment promoting magnetic particles 3 are captured, the dispensing tip 26 is raised along the Z axis to a position above the base plate 14a of the cartridge container 14 while the magnet 46 is still in the vicinity.

In step S8, the nozzle head 15 is further moved in the negative direction of the X axis to thereby move it to the liquid accommodating part 22j, and it is lowered in the Z axis direction in the state where the magnet 46 is in the vicinity of the small diameter tube of the dispensing tip 26 to thereby insert the tip end thereof into the eluate accommodated in the liquid accommodating part 22j. In the state where the magnetic field is being applied, suction/discharging are repeatedly performed, and thereby, the nucleic acid 8 bonded to the magnetic carriers 2 is eluted from the magnetic carriers 2 into the liquid.

Figure 9:
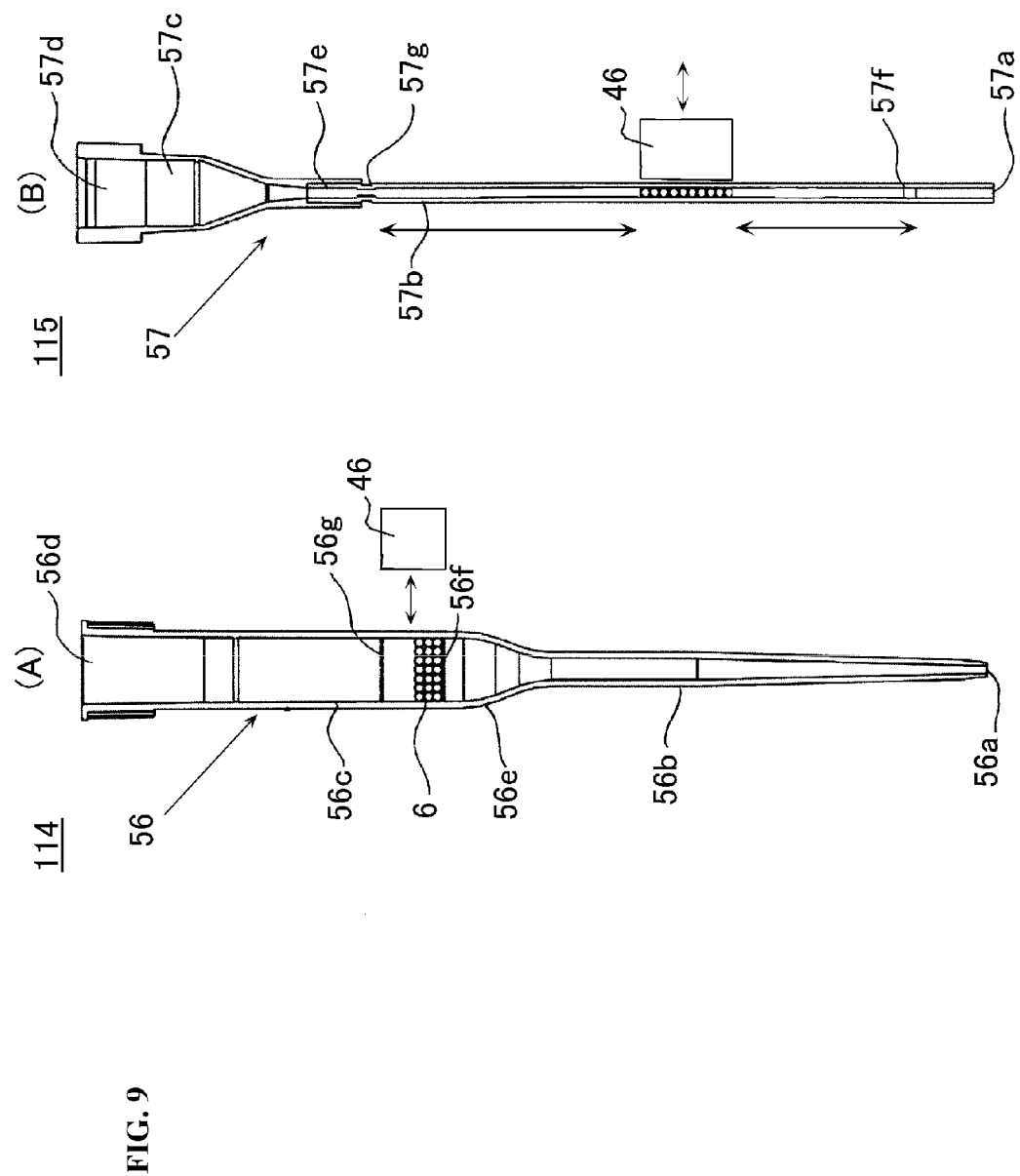
FIG. 9 includes cross sectional views showing an example of a treatment promoting magnetic particle encapsulated tip to be accommodated in a cartridge container for a magnetic reagent according to a third embodiment of the present invention.

FIG. 9 shows a case where the magnet 46 is moved toward and away from treatment promoting magnetic particle enclosure tips 56 and 57 to be accommodated in magnetic reagent cartridge containers 114 and 115 according to two examples of a third embodiment.

In the magnetic reagent cartridge container 114 according to a first example of the third embodiment (FIG. 9(A)), the portion that corresponds to the liquid accommodating part 22a of the cartridge container 14 accommodates a suspension liquid only with magnetic carriers 2 suspended therein instead of the suspension liquid of the magnetic reagent 1, and in the tip accommodating part 21, instead of the dispensing tip 26, there is accommodated a treatment promoting magnetic particle enclosure tip 56, in which treatment promoting magnetic particles 6 are enclosed so as to be able to be moved by a magnetic field.

The treatment promoting magnetic particle enclosure tip 56 according to the first example is such that: there are provided a small diameter tube 56b having an inlet/outlet 56a on the tip end thereof, a large diameter tube 56c that has a diameter greater than that of the small diameter tube 56b, and that has an attachment opening part 56d that can be attached to the nozzle 17, and a transition part 56e that connects the small diameter tube 56b and the large diameter tube 56c; and a plurality (for example, several tens) of the treatment promoting magnetic particles 6 (for example, iron particles of a 1 mm diameter) are enclosed in the large diameter tube 56c so as to be able to be moved by a magnetic field, by a filter 56f that allows liquid to pass therethrough but does not allow the treatment promoting magnetic particles 6 to pass therethrough, and a filter 56g that allows gas to pass therethrough but does not allow the treatment promoting magnetic particles 6 to pass therethrough. The magnet 46 is provided so as to be able to move toward and away from the portion between these two filters 56f and 56g where the treatment promoting magnetic particles 6 are enclosed.

In the magnetic reagent cartridge container 115 according to a second example of the third embodiment (FIG. 9(B)), the portion that corresponds to the liquid accommodating part 22a of the cartridge container 14 accommodates a suspension liquid only with magnetic carriers 2 suspended therein instead of the suspension liquid of the magnetic reagent 1, and in the tip accommodating part 21, instead of the dispensing tip 26, there is accommodated a treatment promoting magnetic particle enclosure tip 57, in which treatment promoting magnetic particles 6 are enclosed so as to be able to be moved by a magnetic field.

The treatment promoting magnetic particle enclosure tip 57 according to the second example is such that: there are provided a small diameter tube 57b with an opening part 57a on the tip end thereof, a large diameter tube 57c that has a diameter greater than that of the small diameter tube 57b, that has an attachment opening part 57d that can be attached to the nozzle 17, and that is formed as a separate body from the small diameter tube 57b, and a transition part 57e that is formed integrally with the large diameter tube 57c and that is formed in a tapered shape; and a plurality (ten in this example) of the treatment promoting magnetic particles 6 are enclosed in a single column form in the small diameter tube 57b. The plurality of treatment promoting magnetic particles 6 are enclosed between two stopping parts 57f and 57g provided in the small diameter tube 57b at an interval greater than the total size of the plurality of the treatment promoting magnetic particles 6 (preferably, twice or more the length of the column of the treatment promoting magnetic particles 6 being in close contact with each other), so that they can be moved along the column direction by the movement of the liquid and the magnetic field without disturbing the order of the column. The stopping parts 57f and 57g are each provided as a depression toward the inner side of the small diameter tube 57b while leaving a gap in the center thereof, by crimping the small diameter tube 57b in a 90-degree-twisting direction such as the front-back direction and left-right direction in the diagram. As a result, both of these allow a liquid to pass therethrough, but they do not allow the particles 6 to pass therethrough. The magnet 46 is provided so as to be able to move toward and away from the small diameter tube 57b near the center of the portion in which these 10 treatment promoting magnetic particles 6 are enclosed.

Figure 10:
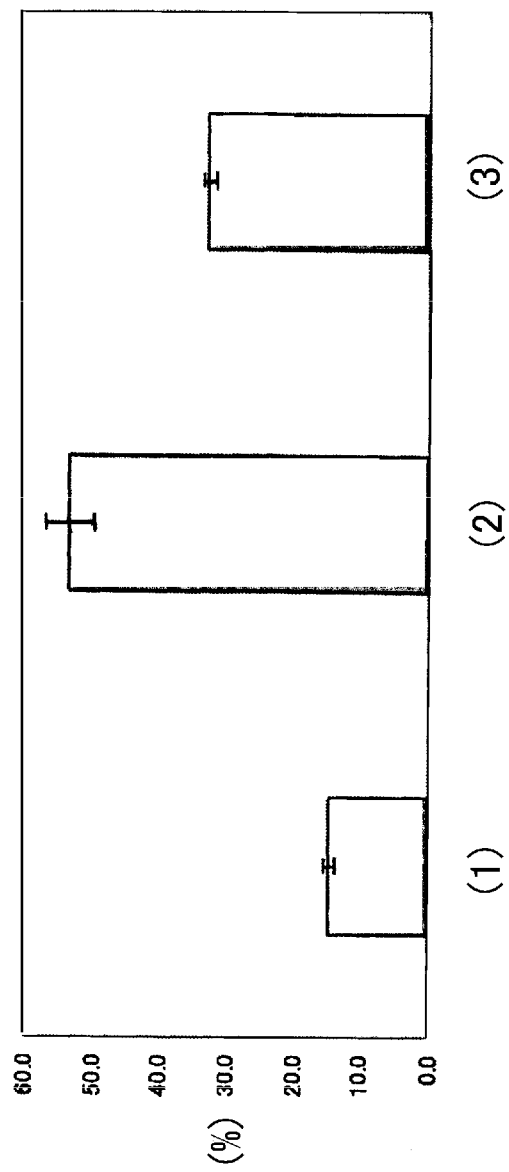
FIG. 10 is a bar chart showing magnetic carrier recovery rates in the case of using a magnetic reagent kit according to the third embodiment of the present invention.

FIG. 10 shows an experiment example of the recovery rate of the magnetic carriers 2 in the case of using the treatment promoting magnetic particle enclosure tip 57 according to the second example of the third embodiment to be accommodated in the magnetic reagent cartridge container 114 that accommodates the magnetic reagent kit. The treatment promoting magnetic particle enclosure tip 57 had twelve iron particles of 1 mm particle diameter enclosed in the small diameter tube 57b so that they could be moved by the movement of the liquid or by a magnetic field. The magnetic reagent cartridge container 114 was such that the liquid accommodating part 22a accommodated a suspension liquid of the magnetic carriers 2 after the dispersion treatment, the liquid accommodating part 22b accommodated 100 μl of distilled water, and the tip accommodating part 21 accommodated the treatment promoting magnetic particle enclosure tip 57.

To make a comparison, as an eleventh magnetic reagent cartridge container 14, the liquid accommodating part 22a accommodated 80 μl of a suspension liquid of the magnetic carriers after the dispersion treatment, the liquid accommodating part 22b accommodated 100 μl of distilled water, and the tip accommodating part 21 accommodated the dispensing tip 26.

Furthermore, in order to make a comparison, as a twelfth magnetic reagent cartridge container 14, the liquid accommodating part 22a preliminarily accommodated 80 μl of a suspension liquid, in which there ware suspended the magnetic carriers after the dispersion treatment, and 8 μl of PSS beads of particle diameter 0.5 μm to 2 μm with a magnetic body $Fe_3O_4$ (190 nm) having cellulose Ac on the surface thereof, and the liquid accommodating part 22b preliminarily accommodated 100 μl of distilled water.

First, the eleventh magnetic reagent cartridge container 14 was loaded in the magnetic carrier treatment device 10, and with use of the dispensing tip 26, the tip end of the dispensing tip 26 was inserted into the liquid accommodating part 22a. When the suspension liquid was suctioned, the magnet 46 was brought into the vicinity of the small diameter tube 26b and a magnetic field was applied to the interior of the small diameter tube 26b, to thereby adsorb the magnetic carriers 2 on the inner wall of the small diameter tube 26b of the dispensing tip 26. While they were still adsorbed, the dispensing tip 26 was moved to the liquid accommodating part 22b, and it was cleaned by performing suction/discharging of the cleaning liquid. Then, the magnet 46 was moved away from the small diameter tube 26b to remove the magnetic field from the interior of the small diameter tube 26b, and suction/discharging were repeatedly performed to thereby suspend the magnetic carriers 2 in the liquid. Accordingly, the residual liquid in the liquid accommodating part 22a was measured on an absorption spectrometer of 480 nm, to thereby calculate the recovery rate of the magnetic carriers 2.

As a result of this, as shown in FIG. 10 (1), it was confirmed that the recovery rate of the magnetic carriers was not more than approximately 20%.

Next, the magnetic reagent cartridge container 114 was loaded in the magnetic carrier treatment device 10, and the nozzle head 15 was moved to attach the treatment promoting magnetic particle enclosure tip 57 accommodated in the tip accommodating part 21 of the magnetic reagent cartridge container 114, to the nozzle. Then, using the enclosure tip 57, the tip end thereof was inserted into the liquid accommodating part 22a, and the magnet 146 was brought to the vicinity of the small diameter tube 57b to apply a magnetic field to the interior of the small diameter tube 57b. Further, suction/discharging of the magnetic carriers 2 was repeatedly performed to adsorb the magnetized magnetic carriers 2 on the magnetized treatment promoting magnetic particles 6 in the small diameter tube 57b of the enclosure tip 57 and on the inner wall thereof, to thereby capture them. The residual liquid in the liquid accommodating part 22a was measured on an absorption spectrometer of 480 nm, to thereby calculate the recovery rate of the magnetic carriers 2. As a result, as shown in FIG. 10 (2), the recovery rate exceeded 50%, and the recovery rate was three times or more the case where the treatment promoting magnetic particles were not present.

To make a comparison, the twelfth magnetic reagent cartridge container 14 was loaded in the magnetic carrier treatment device 10, and using the dispensing tip 26, 8 μl of the suspension liquid containing the magnetic carriers 2 and the treatment promoting magnetic particles accommodated in the liquid accommodating part 22a was repeatedly suctioned/discharged while the magnet 46 was brought to the vicinity of the small diameter tube 26b, to thereby adsorb them on the inner wall of the small diameter tube 26b. Then, the dispensing tip 26 was moved to the liquid accommodating part 22b while they were still adsorbed, and the cleaning liquid was suctioned/discharged to perform cleaning. Accordingly, the residual liquid in the liquid accommodating part 22a was measured on an absorption spectrometer of 480 nm, to thereby calculate the recovery rate of the magnetic carriers 2.

As a result, as shown in FIG. 10 (3), the recovery rate of the magnetic carriers 2 exceeded approximately 30%, and the recovery rate was twice or more the case where the treatment promoting magnetic particles were not present.

Figure 11:
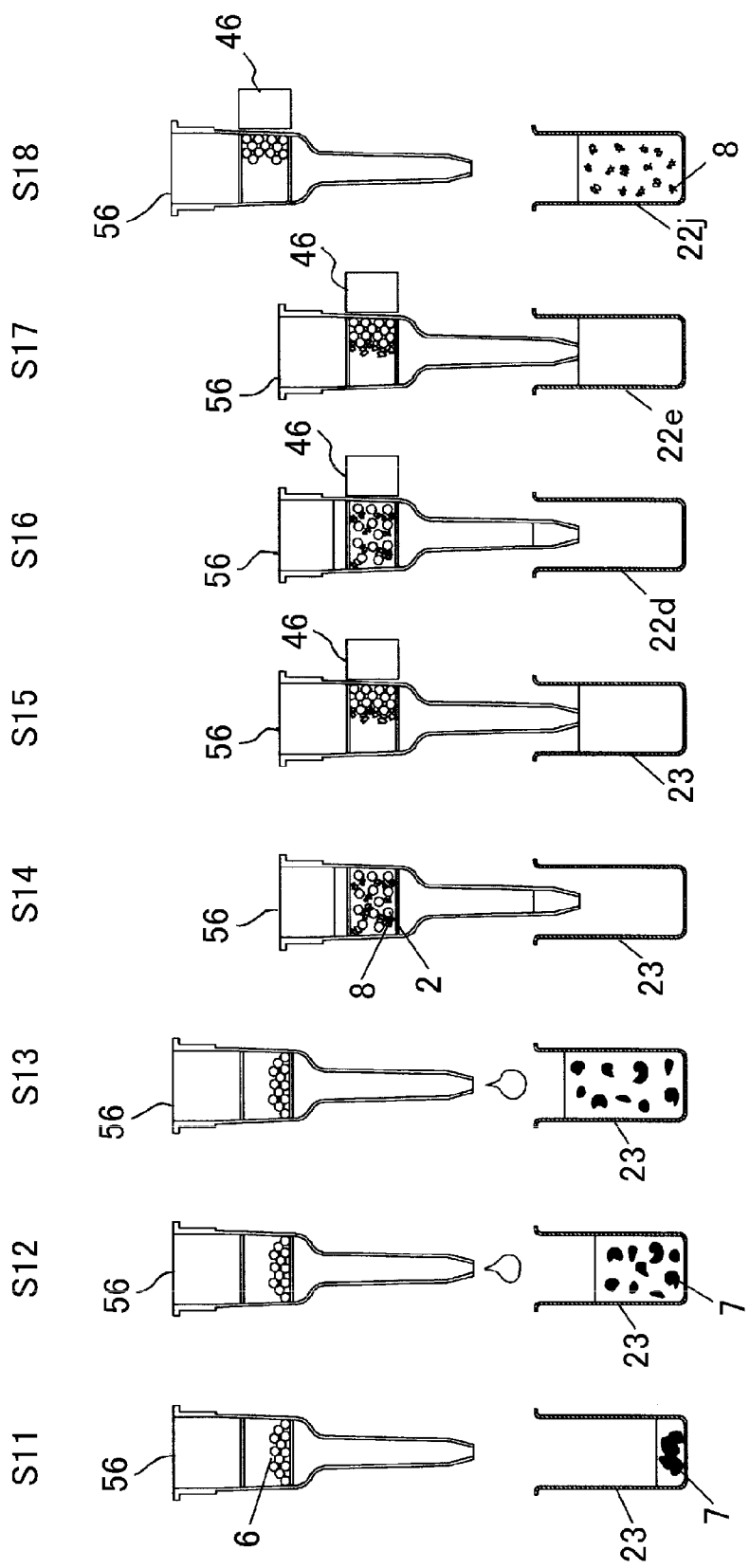
FIG. 11 is a flow chart showing the magnetic reagent kit according to the third embodiment of the present invention with use of the magnetic carrier treatment device according to the second embodiment.

Next, based on FIG. 11, there is shown a flow chart of a treatment for capturing magnetic carriers with use of the magnetic reagent cartridge container 114 (or 115) according to the third embodiment and the above device 10 according to the second embodiment.

The specimen accommodating part 38 of the cartridge container 114 (or 115) accommodates a sample solution containing bacteria 7 preliminarily extracted from a patient as a sample. The liquid accommodating part 22a preliminarily accommodates a suspension liquid of super paramagnetic body magnetic carriers 2 of a nano size particle diameter that are coated with silica for capturing nucleic acid. Moreover, the liquid accommodating part 22b accommodates a lysis buffer liquid for lysing the bacteria 7, the liquid accommodating part 22c accommodates a neutralizing buffer liquid, the liquid accommodating part 22d through the liquid accommodating part 22i accommodate various types of cleaning liquid, and the liquid accommodating part 22j accommodates the eluate.

In step S11, the nozzle head 15 is moved in the positive direction of the X axis, and the nozzle 17 is positioned above the treatment promoting magnetic particle enclosure tip 56 (or 57) held in the cartridge container 114 (or 115). Next, the Z axis movement body 35 is lowered so that the nozzle head 15 is inserted, fitted, and attached into the attachment opening part 56d of the enclosure tip 56 (or 57), and then, it is raised and the tip end of the enclosure tip 56 (or 57) is positioned above the base plate (corresponding to 14a) of the cartridge container 114 (or 115).

Next, the nozzle head 15 is further moved in the positive direction of the X axis to above the specimen accommodating part 38, and the Z axis movement body 35 is lowered to thereby insert the tip end of the enclosure tip 56 (or 57) into the specimen accommodating part 38. Then, part of the sample solution containing the bacteria 7 is suctioned, and having raised the tip end of the enclosure tip 56 (or 57), it is positioned above the base plate of the cartridge container 114 (or 115). Next, the nozzle head 15 is moved along the negative direction of the X axis, to thereby position it above the reaction container 23. By lowering the Z axis movement body 35, the sample liquid is discharged into the reaction container 23.

In step S12, the nozzle head 15 is moved along the positive direction of the X axis to position it above the liquid accommodating part 22b, and it is then lowered along the Z axis to insert the tip end of the enclosure tip 56 (or 57) into the liquid accommodating part 22b, to thereby suction the lysis buffer liquid accommodated in the liquid accommodating part 22b.

Having completed the suction, the enclosure tip 56 (or 57) is raised in the Z axis direction and positioned above the base plate of the cartridge container 114 (or 115), and it is then moved in the negative direction of X axis, to thereby position it above the reaction container 23. The enclosure tip 56 (or 57) is lowered to insert the tip end of the enclosure tip 56 (or 57) into the reaction container 23, and the lysis buffer liquid is discharged into the reaction container 23. By repeatedly performing suction/discharging using the enclosure tip 56 (or 57), the lysis buffer liquid and the sample liquid are agitated. Incubation is performed for a predetermined period of time. As a result, the suspended bacteria 7 and the nuclei of the bacteria 7 are destroyed, and nucleic acid 8 lyses into the liquid containing the lysis buffer liquid.

In step S13, the nozzle head 15 is moved along the positive direction of the X axis to position it above the liquid accommodating part 22c, and it is then lowered along the Z axis to insert the tip end of the enclosure tip 56 (or 57) into the liquid accommodating part 22c, to thereby suction the neutralizing buffer liquid.

Having completed the suction, the enclosure tip 56 (or 57) is raised in the Z axis direction and positioned above the base plate of the cartridge container 114 (or 115), and it is then moved in the negative direction of X axis, to thereby position it above the reaction container 23. The enclosure tip 56 (or 57) is lowered to insert the tip end of the enclosure tip 56 (or 57) into the reaction container 23, and the neutralizing buffer liquid is discharged into the reaction container 23. By repeatedly performing suction/discharging using the enclosure tip 56 (or 57), the neutralizing buffer liquid is agitated with the liquid accommodated in the reaction container 23, to thereby causes it to react with the lysis buffer liquid to neutralize it.

In step S14, the nozzle head 15 is moved in the positive direction of the X axis to position it above the liquid accommodating part 22a, and then, it is lowered along the Z axis to insert the tip end of the enclosure tip 56 (or 57) into the liquid accommodating part 22a for suctioning the magnetic carrier suspension liquid, which is part of the magnetic reagent.

Next, the enclosure tip 56 (57) is raised in the Z axis direction and positioned above the base plate of the cartridge container 114 (or 115), and after having moved the nozzle head 15 in the negative direction of the X axis and positioned it above the reaction container 23, it is lowered in the Z axis direction and the suspension liquid containing the magnetic carriers 2 is discharged into the reaction container 23. The suspension liquid, in which the magnetic carriers 2 are suspended in the solution of the nucleic acid 8 accommodated in the reaction container 23, is suctioned and discharged repeatedly using the enclosure tip 56 (or 57) to thereby agitate it, and the magnetic carriers 2 and the nucleic acid 8 are made to encounter with each other to thereby bond the nucleic acid 8 to the magnetic carriers 2.

In step S15, in the state where the magnet 46 is in the vicinity of the large diameter tube 56c (small diameter tube 57c) of the enclosure tip 56 (or 57), a magnetic field is applied to the interior of the small diameter tube 56b (or the large diameter tube 57c) when suctioning the suspension liquid, to thereby magnetize the magnetic carriers 2 bonded to the nucleic acid 8 in the suspension liquid and the treatment promoting magnetic particles 6 enclosed in the enclosure tip 56 (or 57). As a result, since the particle diameter and the magnetic susceptibility of the treatment promoting magnetic particles 6 dispersed or suspended in the suspension liquid are greater than those of the magnetic carriers 2, the treatment promoting magnetic particles 6 are directly or indirectly attracted to the inner wall of the enclosure tip 56 (or 57), to which the magnet 46 has approached, by a magnetic force greater than that for the magnetic carriers 2, while attracting or adsorbing the magnetic carriers 2 suspended at the periphery thereof. In this state, by repeatedly performing suction/discharging, the magnetic carriers 2 in the suspension liquid can be efficiently captured on the inner wall.

In step S16, in the state where the magnetic carriers 2 and the treatment promoting magnetic particles 6 are captured on the inner wall of the large diameter tube 56c (or the small diameter tube 57b) of the enclosure tip 56 (or 57) while the magnet 46 is in the vicinity of the large diameter tube 56c (or the small diameter tube 57b) of the enclosure tip 56 (or 57), the enclosure tip 56 (or 57) is raised along the Z axis and removed from the reaction container 23, and it is positioned above the cartridge container 114 (or 115). While the magnetic carriers 2 and the treatment promoting magnetic particles 6 in the interior of the enclosure tip 56 (or 57) are still captured on the capturing region, that is, on the inner wall of the enclosure tip 56 (or 57) in this example, it is moved in the positive direction along the X axis and positioned above the liquid accommodating part 22d. While the magnet 46 is in the vicinity of the large diameter tube 56c (or the small diameter tube 57b) of the enclosure tip 56 (or 57), the enclosure tip 56 (or 57) is lowered along the Z axis, to thereby insert the tip end of the enclosure tip 56 (or 57) into the liquid accommodating part 22d. Then, in the state where the magnet 46 is moved away and the magnetic field is removed, the cleaning liquid accommodated in the liquid accommodating part 22d is suctioned/discharged, to thereby clean the magnetic carriers 2 and the enclosed treatment promoting magnetic particles 6.

If necessary, in step S17, the enclosure tip 56 (or 57) is further moved to the liquid accommodating part 22e to thereby perform further cleaning. When the cleaning is complete, while the magnet 46 is in the vicinity of the large diameter tube 56c (or the small diameter tube 57b) of the enclosure tip 56 (or 57), suction/discharging are repeated to thereby capture the magnetic carriers 2 and the treatment promoting magnetic particles 6 on the inner wall of the enclosure tip 56 (or 57). While the magnetic carriers 2 and the treatment promoting magnetic particles 3 are still captured with the magnet 46 in the vicinity, the enclosure tip 56 (or 57) is raised along the Z axis to a position above the base plate of the cartridge container 114 (or 115).

In step S18, the nozzle head 15 is further moved in the negative direction of the X axis to thereby move it to the liquid accommodating part 22j, and it is lowered in the Z axis direction in the state where the magnet 46 is in the vicinity of the small diameter tube of the enclosure tip 56 (or 57) to thereby insert the tip end thereof into the eluate accommodated in the liquid accommodating part 22j. In the state where the magnetic field is being applied, suction/discharging are repeatedly performed, and thereby, the nucleic acid 8 bonded to the magnetic carriers 2 is eluted from the magnetic carriers 2 into the liquid.

Figure 12:
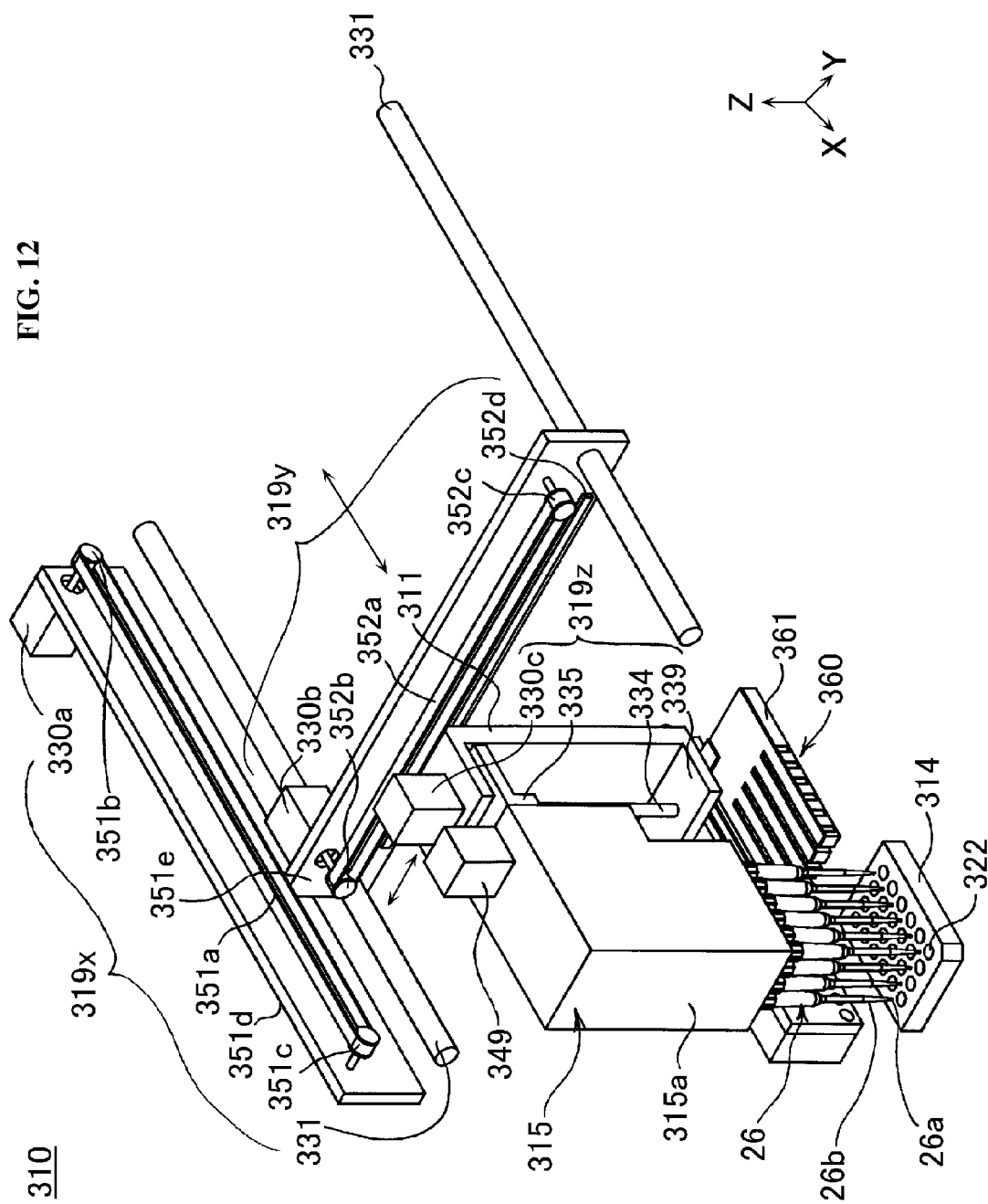
FIG. 12 is a principal perspective view showing a magnetic carrier treatment device according to a fourth embodiment of the present invention.
Figure 14:
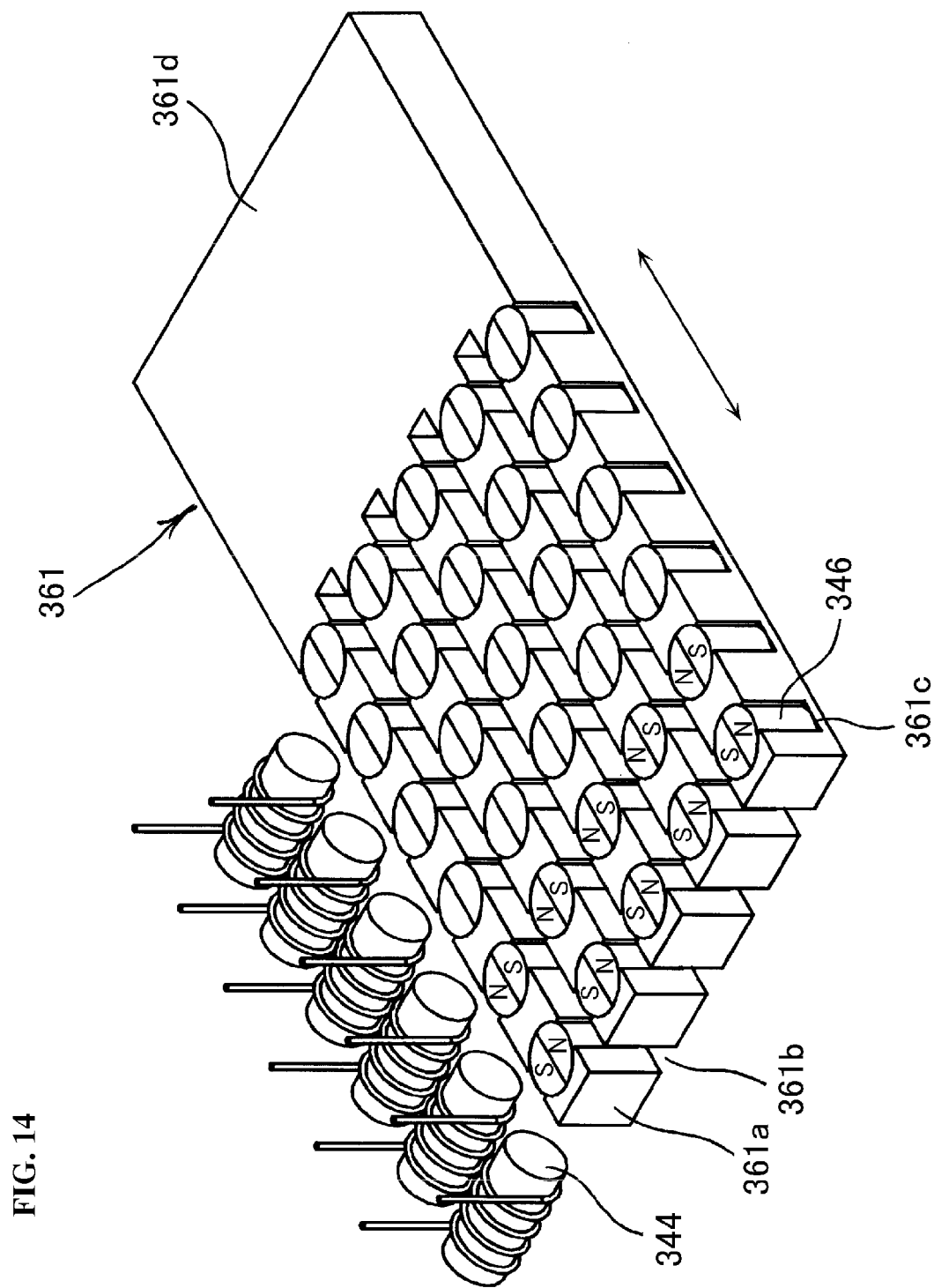
FIG. 14 is a perspective view showing a magnetic device of the magnetic carrier treatment device according to the fourth embodiment of the present invention.

Next, based on FIG. 12 through FIG. 14, a magnetic carrier treatment device 310 according to a fourth embodiment is described. In FIG. 12 and FIG. 13, the casing is removed to facilitate the description of the device interior.

The magnetic carrier treatment device 310 is such that a 24-hole micro plate 314, in which liquid accommodating parts 322 arranged in a matrix form of four rows (extending in the X axis direction) and six columns (extending in the Y axis direction) each accommodating, for example, the magnetic reagent and the magnetic reagent kit according to the first embodiment, is loaded on a stage to be used for treating the magnetic reagent.

The size of the magnetic carrier treatment device 310 excluding the stage is, for example, such that the length is approximately 500-600 mm (X axis direction), the width is approximately 500-600 mm (Y axis direction), and the height is approximately 500-600 mm (Z axis direction). For example, twelve of the micro plates are loaded on the stage to be used. Alternatively, for example, with a 96-hole micro plate, up to eight of them are used.

In one micro plate 314 among the twelve micro plates, there is accommodated a suspension liquid in which a magnetic reagent 1 composed of magnetic carriers 2 and treatment promoting magnetic particles 3 are suspended. The rest of the micro plates accommodate or are able to accommodate various types of reagent, for example, a lysis buffer liquid, a neutralizing buffer liquid, various types of cleaning liquid, a dissociation liquid, and bacteria extracted from 24 types of specimen.

The magnetic carrier treatment device 10 has a nozzle head 315 of a dispensing machine, and a movement mechanism 319 that is capable of moving the nozzle head 315 with respect to the entire range of the stage including the micro plates 314 loaded on the stage.

In FIG. 12, the nozzle head 315 has a head frame body 315a provided thereon, and it has a suction/discharging motor 349 on the upper side thereof. On the lower side thereof, there are provided twenty four dispensing tips 26 in four rows (extending in the X axis direction) and six columns (extending in the Y axis direction) attachably and detachably attached to nozzles 317 communicating with each cylinder, in which a piston is provided so as to be driven by the suction/discharging motor 349 to be able to slide therein. The tip ends 26a of the dispensing tips 26 are provided so as to be able to be inserted into the respective liquid accommodating parts 322 at the same time.

On the nozzle head 315, there are formed a tip column, in which the dispensing tips 26 are attached to a nozzle row with the nozzles 317 arranged along the row direction (X axis direction), and a tip column, in which the dispensing tips 26 are attached to a nozzle row with the nozzles 317 arranged along the column direction (Y axis direction).

The nozzle head 315 of the dispensing machine connects, via a Z axis driving plate 335 that is driven with a Z axis movement ball screw 334 to be able to move in the vertical direction, to an XY axis movement body 311 that is driven by the movement mechanism 319 to move only in the X axis direction and the Y axis direction, and it is capable of moving along the Z axis direction. In the XY axis movement body 311, there is provided a motor 330c that rotatably supports and rotates the ball screw 334, and on the lower side of the bottom plate 339 of the XY axis movement body 311, there is provided a magnetic force device 360 capable of applying and removing a magnetic field to and from the interior of the small diameter tube 26c of the tip 26 attached to the nozzle 317. Moreover, on the stage, there is provided a tip attachment/detachment plate in which a U shape larger than the diameter of the nozzle 317 and narrower than the outer diameter of the thickest portion of the tip 26 is formed in order to attach and detach the tip such as the dispensing tip 26 to and from the nozzle 317.

The movement mechanism 319 has an X axis movement mechanism 319x that moves the XY axis movement body 311 along the X axis direction with respect to the micro plate 314, a Y axis movement mechanism 319y that moves the XY axis movement body 311 along the Y axis direction with respect to the micro plate 314, and a Z axis movement mechanism 319z that moves the nozzle head 315 along the Z axis direction with respect to the XY axis movement body 311.

As shown in FIG. 12, the X axis movement mechanism 319x has an X axis driving motor 330a that is supported on a mechanism supporting plate 351d attached to the main body of the magnetic carrier treatment device 310, a pulley 351b that is rotation-driven by the motor 330a and a pulley 351c that is shaft-supported on the mechanism supporting plate 351d, a timing belt wound on these pulleys 351b and 351c, an X axis driving plate 351e that is connected to this timing belt 351a and is capable of moving along the X axis direction, and two guiding shafts 331 that guide the X axis driving plate 351e.

Moreover, the Y axis movement mechanism 319y has a Y axis driving motor 330b supported on the X axis driving plate 351a, a pulley 352b rotation-driven by the motor 330b and a pulley 352c shaft-supported on the X axis driving plate 351e, a timing belt 352a wound on these pulleys 352b and 352c, the XY axis movement body 311 that is provided on the X axis driving plate 351e, that connects to the timing belt 352a, and that is capable of moving along the Y axis direction, and a guide rail 352d that guides the XY axis movement body 311 along the Y axis direction.

The motor 330c, the Z axis driving plate 335, and the ball screw 334 correspond to the Z axis movement mechanism 319z.

As shown in FIG. 12 and FIG. 13, the magnetic force device 360 has: a magnet array member 361 in which, in order to enable application and removal of a magnetic field to and from the interior of the tips 26 attached to the nozzle 317 and provided so as to be able to move along the row direction (X axis direction) with respect to the tips 26, twenty four cylindrical magnets 346 arranged so as to sandwich each corresponding tip 26 from both sides, are supported and arranged so as to allow them to perform orientation alterations at substantially fixed positions; six electromagnets 344 each serving as a magnetic pole orientation alteration device that is capable of altering the orientation of the magnetic pole of the magnet 346 by applying an orientation alteration magnetic field; an electromagnet supporting plate 343 that is connected to the bottom plate 339, and that has six of the electromagnets 344 arranged in a single column form along the row direction, that is, the X axis direction, so that they are brought adjacent to each tip 26 at the height position of the small diameter tube 26b of the tip attached to the nozzle 317; and a magnet movement mechanism that is indirectly supported on the electromagnet supporting plate 343 and is capable of moving the magnet array member 361.

The magnet movement mechanism has a pulley 342 that is rotation-driven by a motor (not shown in the figure) provided in the electromagnet supporting plate 343 and a pulley 342 shaft-supported on the supporting plate 343, a timing belt wound on these pulleys 341 and 342, a connection part 347 that connects the timing belt 340 and the magnetic arrangement member 361, and a guide rail 348 that guides the connection part 347. Reference symbol 361e denotes a coating plate that prevents the magnets 346 from coming out from the magnet array member 361.

FIG. 14 shows an enlarged view of the magnet array member 361 and the electromagnets 344 according to the fourth embodiment shown in FIG. 13.

The magnet array member 361 has: five comb tooth members 361a having a width that allows at least three nozzles to be inserted between the tip columns, and a length that extends in the direction of the row adjacent to the tips 26 attached to all of 24 nozzles when the nozzles are inserted; and a base part 361d that is formed integrally with the comb-tooth members 361a. In each comb tooth member 361a there are provided six cylindrical magnets 346 that are arranged at column gap intervals and in positions that correspond to each of the tips 26 attached to each nozzle when they are brought to the vicinity of the tips 26, and a pair of two corresponding magnets sandwich from both sides each tip 26 inserted in the gap 361b formed between each of two adjacent comb tooth members 361a so that the different magnetic poles face each other.

That is to say, the magnet array member 361 has a total of twenty four cylindrical magnets 346 that, in pairs of two, correspond redundantly to the respective tips 26, and substantially cylindrical bottom ended holes 361c for supporting and arranging the magnets 346 so that orientation alterations can be performed at a substantially fixed position. The side walls of the hole 361c that come into the closest vicinity of the respective tips 26 are removed sufficiently enough to keep the magnet 346 from coming off, allowing the magnet 346 to come into the vicinity of the tip 26. The hole 361c has a radius that substantially enables smooth rotation of the accommodated magnet 346 about the rotational symmetric axis thereof.

When the magnets 346 are in the vicinity of each tip 26, the electromagnet 344 applies an orientation alteration magnetic field to thereby alter the orientation of the magnetic poles or reverse the magnetic poles for each tip 26, so that the different magnetic poles of a pair of two magnets 346 are arranged so as to face each other and sandwich the tip 26 from both sides. The magnets 346 are formed in a cylindrical (body of rotation) shape, and therefore, they rotate about the rotational symmetry axis thereof and orientation alteration and reversal of the magnetic poles are performed at a substantially fixed position.

By applying an orientation alteration magnetic field of the electromagnets 344 for each magnet, the respective magnets 346 arranged in the comb tooth member 361a closest to the six electromagnets 344 are reversed or orientation-altered first. Consequently, with the reversal or orientation alteration of the respective magnets 346, the magnets 346 of each comb tooth member 361a are sequentially reversed or orientation-altered in a chain-reaction like manner. As a result, magnetic field alterations are given to the interior of each tip 26, and thereby the movement of the magnetic carriers or the treatment promoting magnetic particles accommodated in the tip 26 are altered and agitation thereof can be performed.

Figure 15:
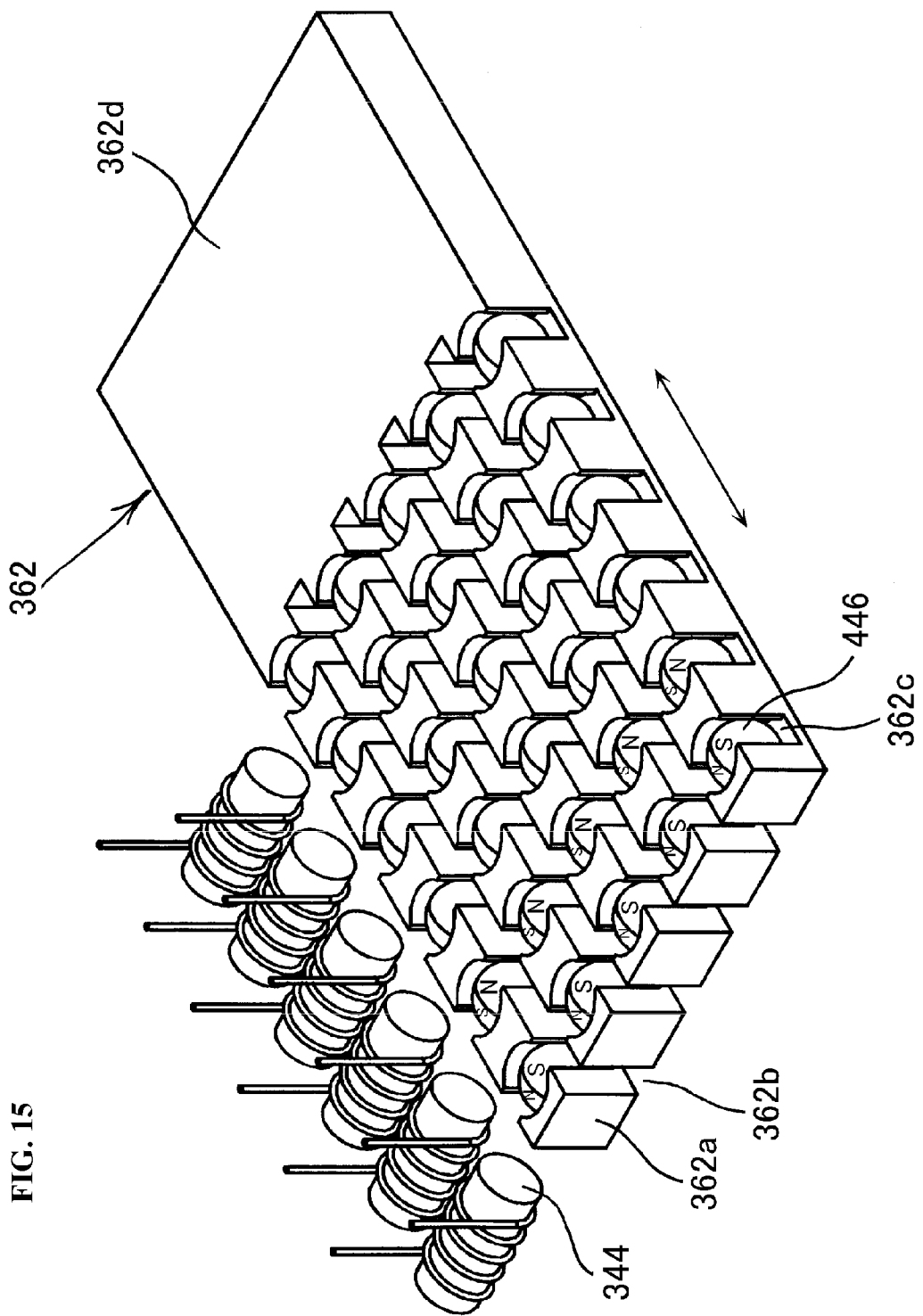
FIG. 15 is a perspective view showing a magnetic device of a magnetic carrier treatment device according to a fifth embodiment of the present invention.

FIG. 15 shows a magnet array member 362 according to a fifth embodiment and the electromagnet 344. The magnet array member 362 is to be used to replace the magnet array member 361 according to the fourth embodiment in the device 310 shown in FIG. 13. The magnet array member 362 differs from the magnet array member 361 in that spherical magnets 446 are used instead of cylindrical magnets 346. The spherical magnets 446 are accommodated in twenty four substantially cylindrical holes 362c that accommodate the magnets 446 so that the orientation of the magnetic poles thereof can be altered. When the spherical magnets 446 are in the vicinity of each tip 26, the electromagnet 344 applies an orientation alteration magnetic field to thereby alter the orientation of the magnetic poles or reverse the magnetic poles for each tip 26, so that the different magnetic poles of a pair of two magnets 446 are arranged so as to face each other and sandwich the tip 26 from both sides. Since the magnet 446 is formed in a spherical shape, orientation alteration and reversal of the magnetic poles are performed at a substantially fixed position. Since the spherical magnet 446 has a smaller area in contact with the hole 362c compared to that of the cylindrical magnet 346, orientation alterations and reversals are performed smoothly. Other aspects are similar to those described with the magnet array member 361.

Figure 16:
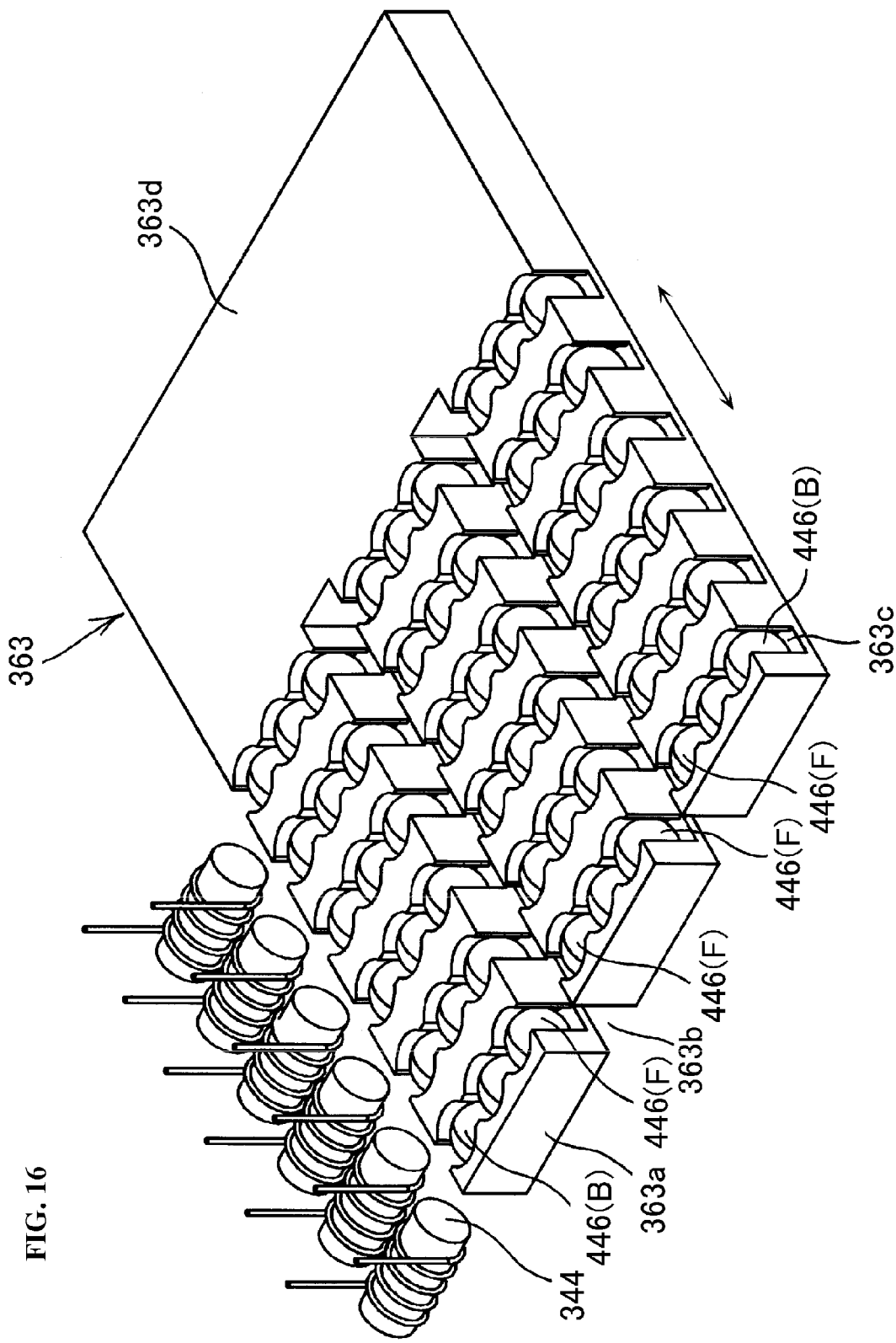
FIG. 16 is a perspective view showing a magnetic device of a magnetic carrier treatment device according to a sixth embodiment of the present invention.

FIG. 16 shows a magnet array member 363 according to a sixth embodiment and the electromagnets 344. The magnet array member 363 is such that there are provided: a total of fifty four spherical magnets 446 that, in sets of six, correspond redundantly to the respective tips 26 so as to be able to apply and remove a magnetic field to and from the interiors of twelve tips 26 attached to a nozzle head (not shown in the figure) having twelve nozzles 317 in two rows (extending in the X axis direction) and six columns (extending in the Y axis direction) at the same time; and connection channels 363c, whereby three substantially cylindrical vertical holes that accommodate the spherical magnets 446 so as to enable orientation alterations at a substantially fixed position are connected along the Y axis direction, provided along the X axis direction (row direction). A set of six magnets 446 for each tip 26 includes two magnet groups each consisting of three magnets, and each magnet groups consists of three magnets 446 arranged at predetermined intervals in a single column form (the column direction=along the Y axis direction).

When in the vicinity of each tip 26, the magnets 446 that belong to a set of two magnet groups for each tip 26, are arranged in a single column form along the Y axis direction so as to sandwich the tip 26 from both sides. When the magnet array member 363 is moved so that two tip end magnets 446 (F) of two magnet groups sandwich the tip 26 from both sides, the electromagnet 344 serving as the magnetic pole orientation alteration device orientation-alters or reverses the magnetic poles of rear end magnets 446 (B) of each group by applying an orientation alteration magnetic field thereto, and thereby the magnetic poles of the tip end magnets 446 (F) are orientation-altered or reversed in a chain-reaction manner, to thereby alter the movement of the magnetic field applied to the interior of the tip 26.

The magnet array member 363 has: three comb tooth members 363a that are provided so as to move along the row direction (X axis direction), and that have a width that allows a single nozzle to be inserted between the tip columns, and a length that extends fully in the direction of the row adjacent to the tips 26 attached to all of twelve nozzles when the tips 26 are inserted; and a base part 363d that is formed integrally with the comb-tooth members 363a. In each comb tooth member 363a, there are provided along the X axis direction six connection channels 363c that are arranged at column gap intervals in positions corresponding to the respective tips 26 when in the vicinity of the tips 26 attached to the nozzles. There are provided a set of two magnet groups that sandwich each tip 26 inserted in the gap 363b formed between the two adjacent comb tooth members 363a, so that the different magnetic poles thereof face each other.

Figure 17:
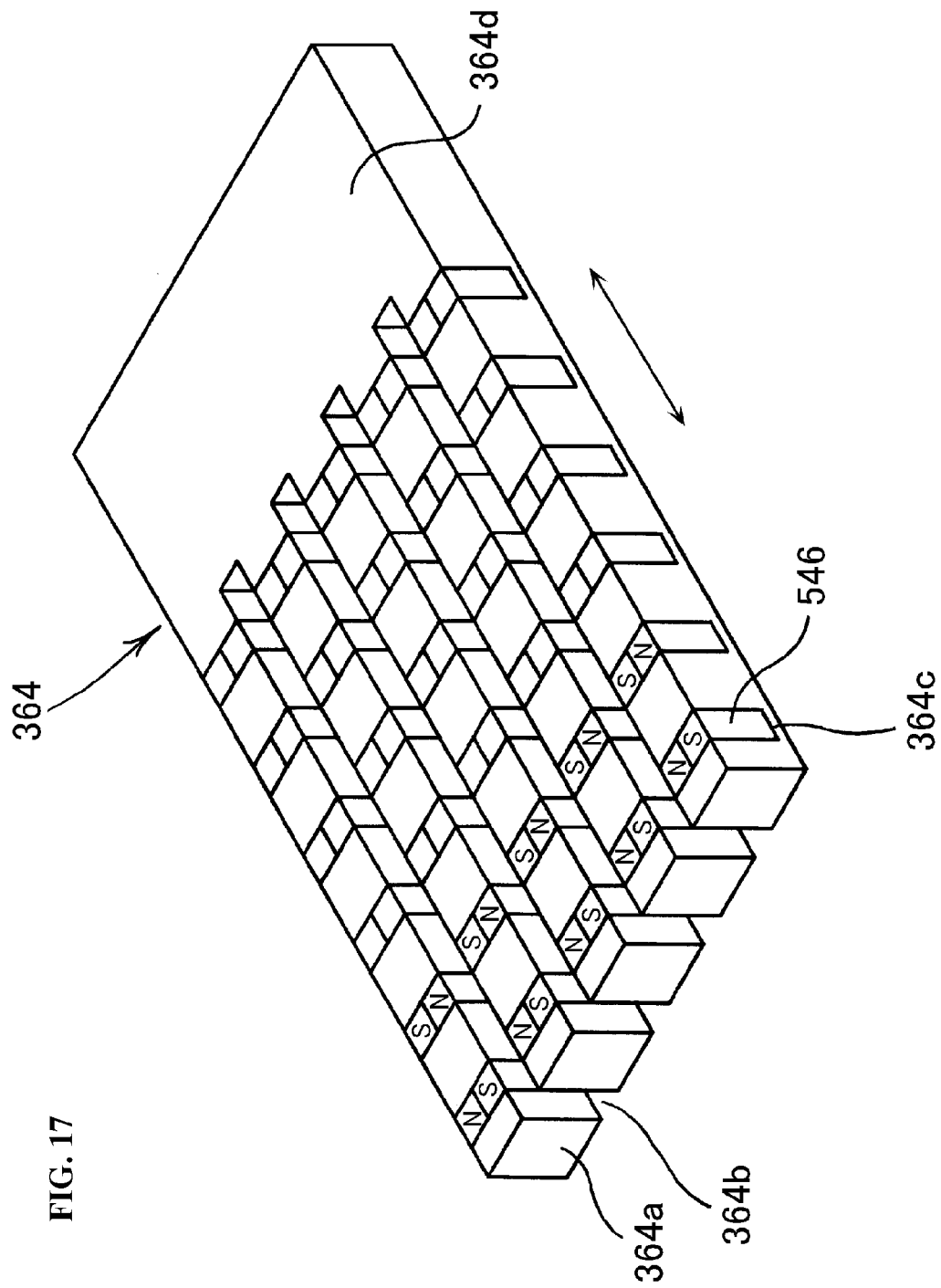
FIG. 17 is a perspective view showing a magnetic device of a magnetic carrier treatment device according to a seventh embodiment of the present invention.

FIG. 17 shows a magnet array member 364 according to a seventh embodiment. The magnet array member 364 has a total of twenty four block magnets 546 that, in pairs of two, correspond redundantly to the respective tips 26 so as to be able to apply and remove a magnetic field to and from the interiors of twenty four tips 26 attached to the nozzle 317 at the same time; and twenty four bottom-ended slit holes 364c, into which the magnets 546 are fitted so as to disable orientation alteration at a substantially fixed position.

The magnets are arranged so that, with respect to each tip 26, the different magnetic poles of a pair of two magnets 546 sandwich each tip 26 from both sides and face each other, when the magnet array member 364 is in the vicinity of each tip 26.

As shown in FIG. 17, the magnet array member 364 is provided so as to be able to move along the row direction (X axis direction). The magnet array member 364 has: five comb tooth members 364a having a width that allows at least three nozzles to be inserted between the nozzle rows, and a length that extends fully in the direction of the row adjacent to the tips 26 attached to all of twenty four nozzles when the tips 26 are inserted; and a base part 364d that is formed integrally with the five comb-tooth members 364a. In each comb tooth member 364a, there are provided six block magnets 546 that are arranged at column gap intervals and in positions corresponding to each of the tips 26 when they are in the vicinity of the respective tips, and a pair of two corresponding magnets 546 sandwich from both sides of each tip 26 inserted in the gap 364b each formed between two adjacent comb tooth members 364a so that the different magnetic poles face each other.

Figure 18:
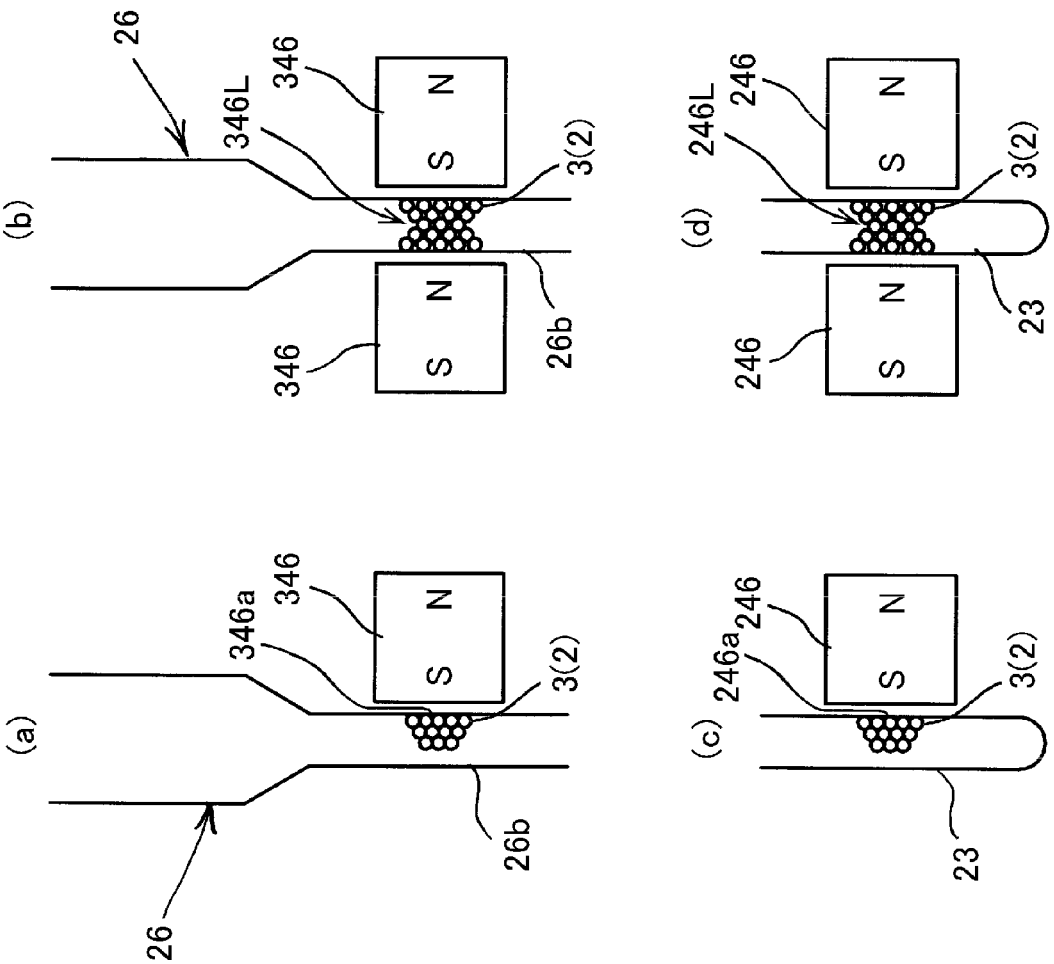
FIG. 18 is an operation explanation diagram of the magnetic carrier treatment device according to the embodiments of the present invention.

FIG. 18 (a) and FIG. 18 (c) respectively show a state of magnetic carriers 2 or treatment promoting magnetic particles 3 in the small diameter tube 26b of the tip 26 or in the container 23 when the magnet 346 is brought from one side to the vicinity of the small diameter tube 26b of the tip 26 attached to the nozzle 317 or the container 23. In this case, there is shown a state where the magnetic carriers 2 are adsorbed only on the capturing regions 346a and 246a of the inner wall on the magnets 246, 346 side.

FIG. 18 (b) and FIG. 18 (d) respectively show the state of magnetic carriers 2 or treatment promoting magnetic particles 3 in the small diameter tube 26b of the tip 26 or in the container 23 when two magnets 346 are brought from both sides to the vicinity so that the different magnetic poles thereof face each other. In this case, there is shown a state where the magnetic carriers are forming filter-like particle layers 346L and 246L so as to partition the interior of the small diameter tube 26b or the container 23.

Figure 19:
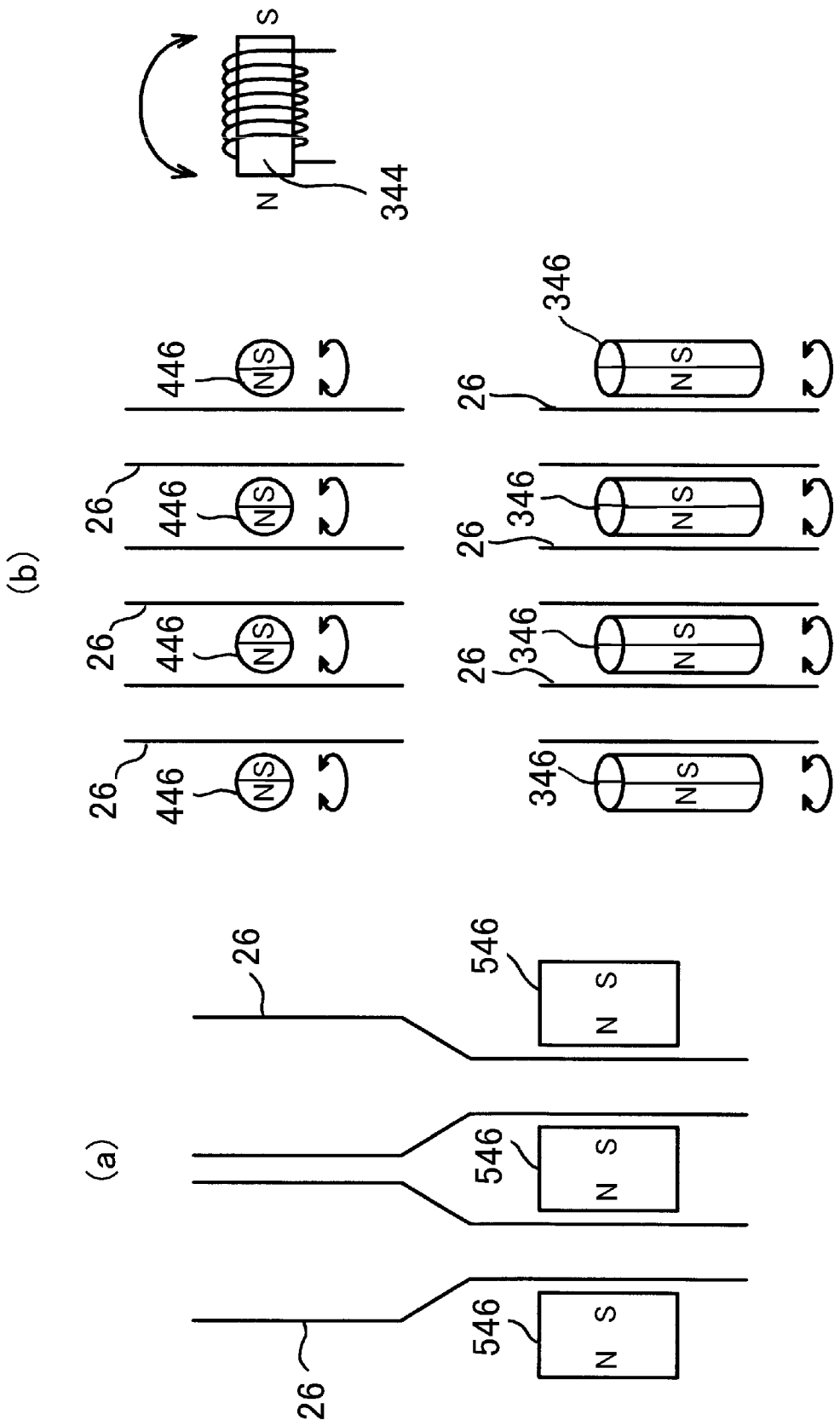
FIG. 19 is an operation explanation diagram of the magnetic carrier treatment device according to the embodiments of the present invention.

FIG. 19 (a) shows that the magnetic poles of the block magnets 546 in the vicinity of the tip 26 are fixed and the orientation thereof is not altered, and FIG. 19 (b) shows an operation in which the magnetic poles of the spherical magnets 446 are sequentially rotated 180 degrees and reversed (orientation-altered) at the respective positions by the orientation alteration magnetic field of the electromagnets 344 serving as magnetic pole orientation alteration devices. FIG. 19(b) schematically shows an operation in which the respective cylindrical magnets 346 are sequentially rotated 180 degrees and reversed (orientation-altered) about the rotational symmetry axis at each fixed position by the orientation alteration magnetic field.

Each of the embodiments described above is specifically described to facilitate better understanding of the present invention, and it is not to limit other embodiments. Therefore, modifications may be made thereto without departing from the scope of the invention. For example, the size of the magnetic carriers is not limited to a nano size, and it may be a micro size. Moreover, also the size of the treatment promoting magnetic particles may be a nano size. In addition, the numerical values, frequencies, shapes, numbers, and quantities used in the above description are not limited to those in the description. Furthermore, the flow tube, in which the treatment promoting magnetic particles are enclosed, may be provided as part of another column or flow tube of the tip that is attachable/detachable. Moreover, the magnetic reagent or the kit thereof may also be enclosed in a micro plate, in addition to the cartridge container.

In the above examples, there have been described those cases where magnetic carriers and treatment promoting magnetic particles are directly or indirectly adsorbed on the inner wall of the container or the tip serving as a capturing region. However, it is not limited to these cases, and they may be captured by directly or indirectly adsorbing them on the surface of a member with a built-in magnet inserted in the container or the tip. In this case, the surface of the member serves as a capturing region.

There has been described the case where the magnet array member of the magnetic force device applies a magnetic field to tips arranged in a matrix form. However, a magnetic field may be applied to liquid accommodating parts arranged in a matrix form. Moreover, a magnetic field may be applied to tips or liquid accommodating parts arranged in a single column form or a single row form, or to a single tip or a single liquid accommodating part. The spatial relationship between "column", "row", "X axis", "Y axis", and "Z axis" is not fixed to those illustrated in the figures. Furthermore, the various types of substances, the various types of components, and the various types of steps used in the magnetic carrier treatment device or the magnetic carrier treatment method in the above description such as the magnetic carriers, the treatment promoting magnetic particles, and various types of reagents, the containers, the liquid accommodating parts, the nozzle heads, the tips, the movement mechanisms, the magnetic force devices, the tip attachment/detachment mechanisms, the magnets, the magnet array members, the comb tooth members, and the motors, and the contact step, capturing step, the separation step, the particle layer formation step, the mixing step, and the movement alteration step, may have necessary modifications made thereto and may be mutually combined.

INDUSTRIAL APPLICABILITY

The present invention relates to a magnetic carrier treatment device and a treatment method thereof, and may be utilized particularly in various fields including the areas where handlings of biological macromolecules and biological low macromolecules such as genes, immune systems, amino acids, proteins, and sugars, are required, such as biochemistry areas, industrial areas, agricultural areas including food processing, agrotechny, and fishery processing, pharmaceutical areas, and medical areas such as hygiene, healthcare, immunity, pathology, and genetics.

DESCRIPTION OF REFERENCE SYMBOLS

1: Magnetic reagent
2: Magnetic carrier
3, 6: Treatment promoting magnetic particle
10, 310: Magnetic carrier treatment device
14, 114, 115: Magnetic reagent cartridge container
15, 315: Nozzle head
17, 317: Nozzle
26: Dispensing tip
46, 146, 246, 346, 446, 546: Magnet
46a, 46b, 146a, 246a: Capturing region
56, 57: Treatment promoting magnetic particle enclosure tip
60, 360: Magnetic force device

The invention claimed is:

1. A magnetic reagent kit having:
a plurality of magnetic carriers that are magnetizable by exposure to a magnetic field, and bonded, in a liquid, to either a predetermined chemical substance or a living organism, said magnetic carriers each having a particle diameter that enables it to be suspended in the liquid;
a plurality of treatment promoting magnetic particles that are magnetizable by exposure to the magnetic field so that said magnetic carriers are adsorbable on respective surfaces thereof, said treatment promoting magnetic particles being formed so as to be suspended, or dispersed, within said liquid by the magnetic field, or by movement of said liquid, to promote a treatment for capturing or re-suspension of said magnetic carriers; and
a cartridge container having one or more liquid accommodating parts and one or more tip accommodating parts, the one or more liquid accommodating parts defining an opening part sealed with a perforatable thin film, the one or more tip accommodating parts containing a dispensing tip and a perforation tip by which the perforatable thin film is perforatable, and the dispensing tip having a capturing region on which the magnetic carriers and the treatment promoting magnetic particles are adsorbable by exposure to the magnetic field,
wherein the treatment promoting magnetic particles have a magnetic flux density higher than that of the magnetic carriers, and are provided so as not to be bonded, in the liquid, to either the predetermined chemical substance or the living organism,
wherein the magnetic carriers are accommodated within at least one of the one or more liquid accommodating parts, and the treatment promoting magnetic particles are accommodated within the at least one of the one or more liquid accommodating parts, or at least another one of the one or more liquid accommodating parts,
wherein the plurality of treatment promoting magnetic particles, the plurality of magnetic carriers, and either the predetermined chemical substance or the living organism, are mixable in the liquid to form a mixture, said mixture being suctioned and discharged by the dispensing tip, and
wherein, during the suctioning and discharging of the mixture by the dispensing tip, the mixture is exposed to the magnetic field so that the treatment promoting magnetic particles and the magnetic carriers are adsorbed on the capturing region of the dispensing tip.

2. The magnetic reagent kit according to claim 1, wherein a particle diameter of said treatment promoting magnetic particles is greater than that of said magnetic carriers.

3. The magnetic reagent kit according to claim 1, wherein a particle diameter of said treatment promoting magnetic particles is in a range of 0.001 mm to 5 mm.

4. The magnetic reagent kit according to claim 3, wherein a magnetic susceptibility of said treatment promoting magnetic particles is greater than that of said magnetic carriers at normal temperature.

5. The magnetic reagent kit according to claim 1, wherein said treatment promoting magnetic particles have a ferromagnetic body, and said magnetic carriers have a paramagnetic body or a super paramagnetic body.

6. The magnetic reagent kit according to claim 1, wherein said treatment promoting magnetic particles are formed with a size or from a material different from that of said magnetic carriers.

7. The magnetic reagent kit according to claim 2, wherein a magnetic susceptibility of said treatment promoting magnetic particles is greater than that of said magnetic carriers at normal temperature.

8. The magnetic reagent kit according to claim 1, wherein the treatment promoting magnetic particles adsorbed on the capturing region expand an effective reaching range of the magnetic field.

* * * * *